(12) United States Patent
Quijano et al.

(10) Patent No.: US 10,973,633 B2
(45) Date of Patent: Apr. 13, 2021

(54) VALVED STENT FOR ORTHOTOPIC REPLACEMENT OF DYSFUNCTIONAL CARDIAC VALVE AND DELIVERY SYSTEM

(71) Applicant: NAVIGATE CARDIAC STRUCTURES, INC., Lake Forest, CA (US)

(72) Inventors: Rodolfo C. Quijano, Laguna Hills, CA (US); Ryan Bertwell, Irvine, CA (US)

(73) Assignee: NAVIGATE CARDIAC STRUCTURES, INC., Lake Forest, CA (US)

(*) Notice: Subject to any disclaimer, the term of this patent is extended or adjusted under 35 U.S.C. 154(b) by 0 days.

(21) Appl. No.: 16/691,502

(22) Filed: Nov. 21, 2019

(65) Prior Publication Data

US 2020/0155307 A1 May 21, 2020

Related U.S. Application Data

(63) Continuation-in-part of application No. 16/613,761, filed as application No. PCT/US2018/032615 on May 14, 2018.

(60) Provisional application No. 62/505,964, filed on May 14, 2017.

(51) Int. Cl.
*A61F 2/24* (2006.01)

(52) U.S. Cl.
CPC .......... *A61F 2/2418* (2013.01); *A61F 2/2436* (2013.01); *A61F 2/2445* (2013.01)

(58) Field of Classification Search
CPC .... A61F 2/2409; A61F 2/2418; A61F 2/2436; A61F 2/2442
See application file for complete search history.

(56) References Cited

U.S. PATENT DOCUMENTS

| | | | |
|---|---|---|---|
| 10,856,858 B2* | 12/2020 | Thambar | A61B 17/0057 |
| 2012/0078353 A1* | 3/2012 | Quadri | A61F 2/2418 623/2.11 |
| 2016/0100940 A1* | 4/2016 | Dwork | A61F 2/2427 623/2.11 |
| 2016/0235529 A1* | 8/2016 | Ma | A61F 2/2418 |
| 2016/0310268 A1* | 10/2016 | Oba | A61F 2/2418 |
| 2017/0231765 A1* | 8/2017 | Desrosiers | A61F 2/966 623/2.11 |

* cited by examiner

*Primary Examiner* — Sarah W Aleman
(74) *Attorney, Agent, or Firm* — Kurt T. Mulville; VLP Law Group, LLP

(57) ABSTRACT

This invention discloses a valved stent for implantation at a dysfunctional or diseased atrioventricular valvular annulus. The valved stent is expandable from a collapsed shape to an expanded shape for minimally invasive delivery and has a low profile at the atrial or superior aspect to achieve improved hemodynamics and offers the capability to fabricate replacement valves having large diameters, The invention also includes a delivery apparatus uniquely designed for implantation of the valved stent and offering the potential for controlled and precise placement of the valved stent at the atrioventricular annulus. The invention also includes methods for use of the above devices and for treating diseased atrioventricular valves.

17 Claims, 19 Drawing Sheets

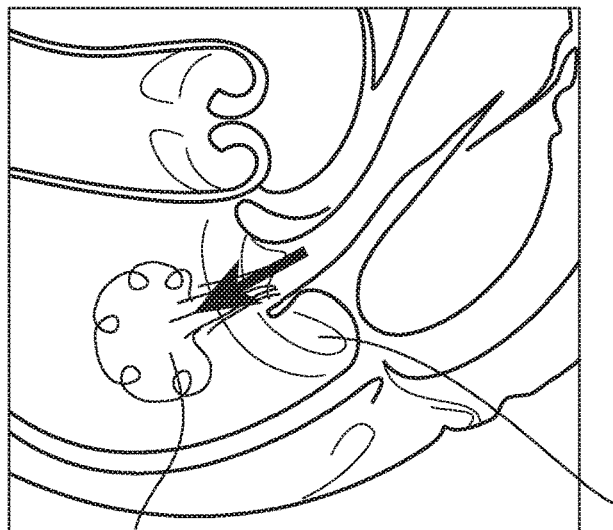
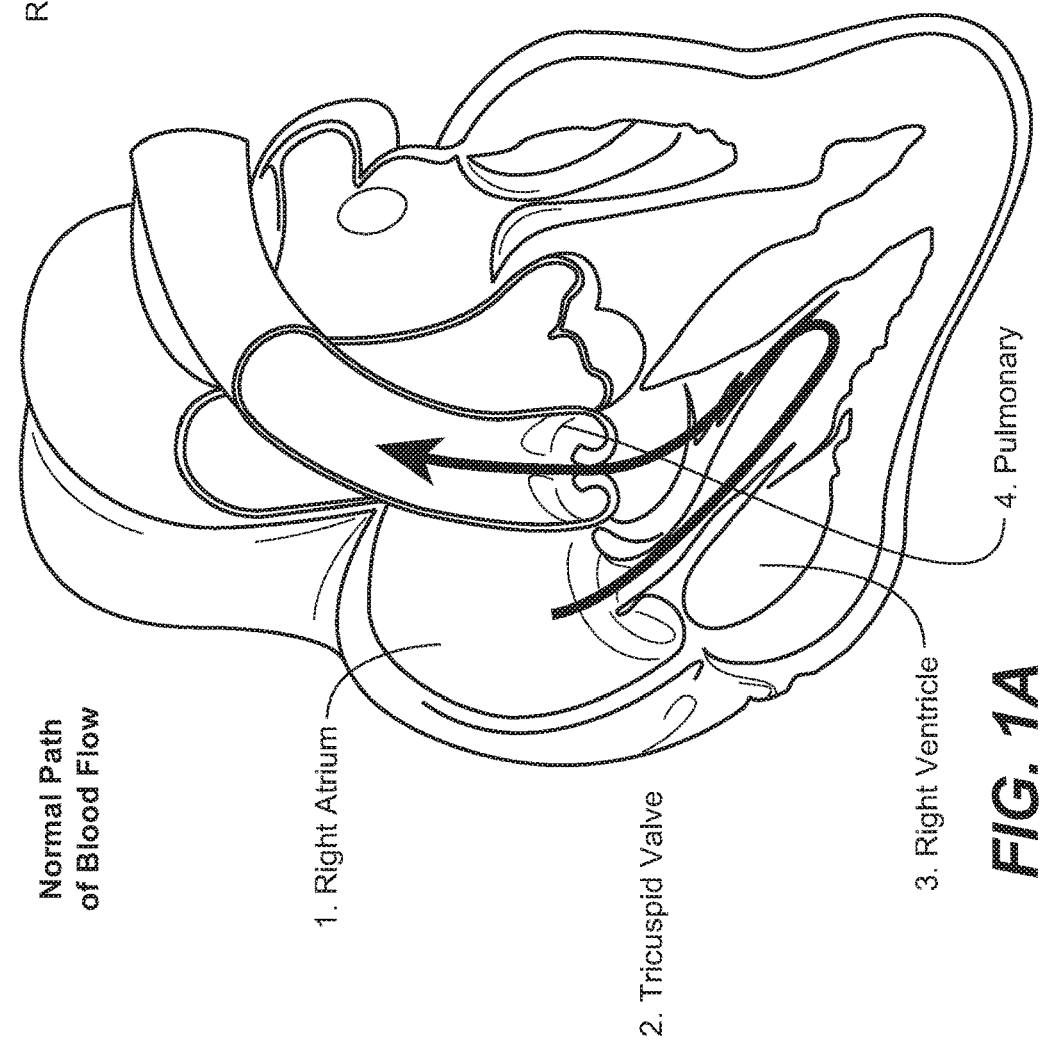

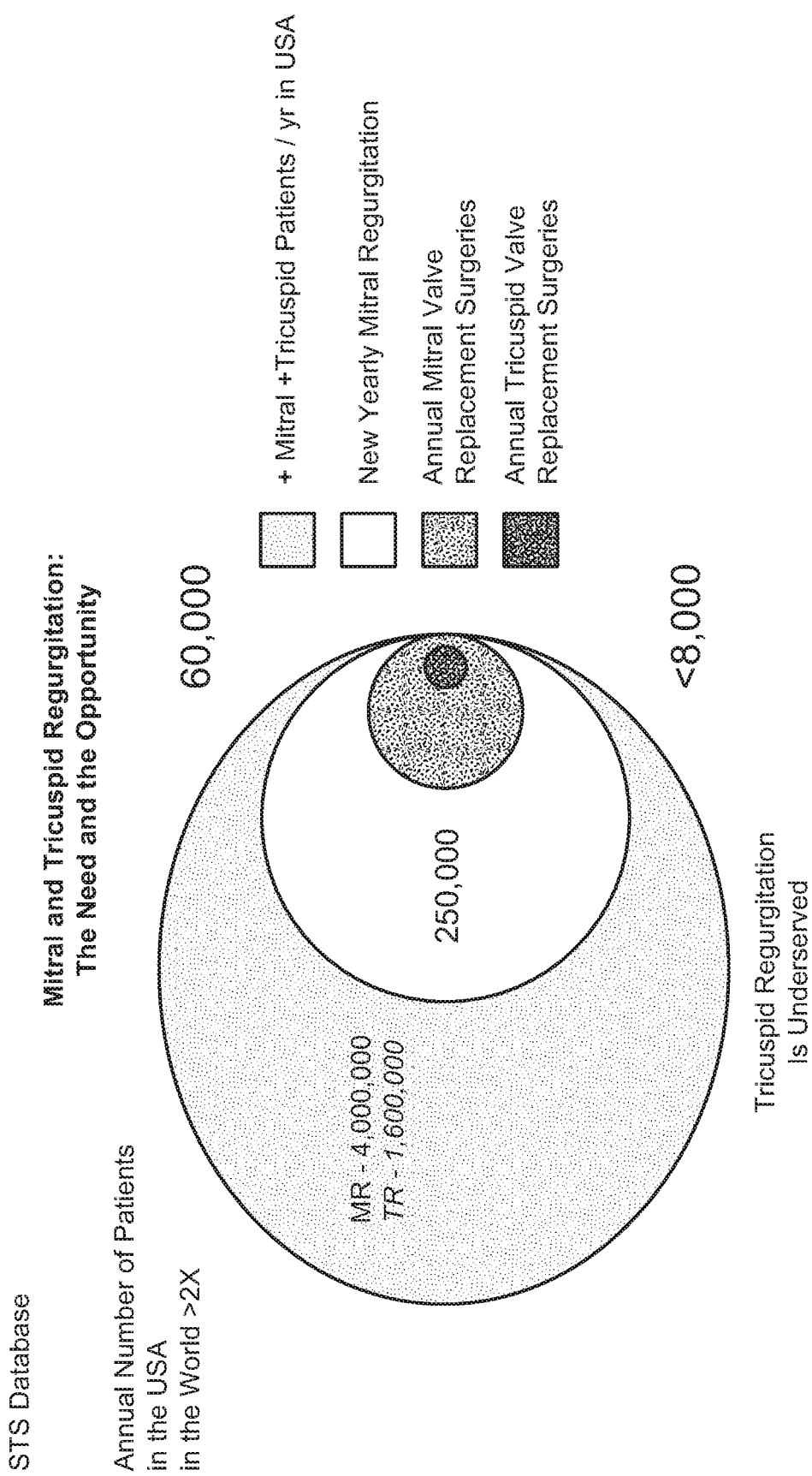

VALVED STENT FOR ORTHOTOPIC REPLACEMENT OF DYSFUNCTIONAL CARDIAC VALVE AND DELIVERY SYSTEM

CROSS-REFERENCE TO RELATED APPLICATIONS

This application is a continuation in part of U.S. application Ser. No. 16/613,761, filed Nov. 14, 2019, which is a a national phase entry from International Patent Application PCT/US2018/032615, filed May 14, 2018, which claims priority to Provisional Patent Application No. 62/505,964, filed May 14, 2017, both incorporated by reference herein.

FIELD OF THE INVENTION

This invention discloses a valved stent for the replacement and restoration of normal function in defective heart valves and a specific system and methods for delivery and deployment of the valved stent as a prosthetic heart valve under controlled conditions enabled by the unique structure and function of the prosthetic valve. More specifically, the invention discloses preferred geometries and critical dimensions for the structure of prosthetic valves when anchored to the native valve annulus to improve fluid dynamics through the prosthetic valve and proximate vasculature and unique methods of deployment of the valve using minimally invasive surgery. The invention also includes a transluminal delivery system and methods for use thereof that deploys the replacement prosthetic valves using optimal positioning techniques using the structure of the prosthetic paired with the delivery system to assure proper attachment at the native annulus to improve subsequent cardiac function of the patient while minimizing surgical complications.

BACKGROUND OF THE INVENTION

The four valves found in a normal heart, the pulmonary, aortic, tricuspid, and mitral valves, have specific form and function. The primary function of all four valves is to maintain unidirectional blood flow by opening and closing at coordinated and specific times during the cycle of the beating heart. In this manner, blood is collected from all tissues of the body and returned through the veins to the right side of the heart through the right atrium (RA) and passes through the tricuspid valve. This valve, the entry gate to the heart, is part of a integrated physiological structure formed from the area surrounding the valve termed the "annulus" a poorly defined area attached to three valve leaflets of different shape that have no free edges as are found in the aortic and pulmonic valves. The edges of the tricuspid valve are also attached to chordae tendinae (literally "tendinous cords") that act as fibrous strands to attach to the valve to the walls (or "myocardium") of the heart muscle opposite to or on the distal side. Together these components function to maintain the proper function and structural conformation of the valve when opening and closing during the regulated blood flow process where the heart pumps blood throughout the body.

The chordae tendinae are an important structural component of the heart and protect the leaflets of the valve from bursting or reverting when the ventricle pumps blood forward, and thereby prevents valve failure that would lead to an inadequate volume of blood reaching the lungs. Accordingly, as the right ventricle contracts and pushes blood forward, the tricuspid valve must close behind the flow to maintain competency to ensure that most of the blood volume within the ventricle is pushed through the pulmonary valve to reach the lungs for oxygenation.

Continuing in a unidirectional flow, the oxygenated blood flow then enters the left side of the heart through the left atrium and subsequently the left ventricle through another atrioventricular valve known as the "mitral valve." Similar to the tricuspid valve, the leaflets of the mitral valve are attached to an annulus at the atrial side and to chordae tendinae on the ventricular side that are attached to the myocardium of the left ventricle (LV) and in the same manner as with the tricuspid valve. When the mitral valve is closed, the left ventricle then contracts to propel oxygenated blood through the aorta to every tissue in the body.

To provide enough oxygenated blood flow throughout the entire body, the pumping action of the left ventricle must reach magnitudes larger than that of the right ventricle, as can be seen by the difference in magnitude of the ventricles instantaneous pressure which can be expressed mathematically as a change in pressure as a function of time (dp/dt). The left ventricle differential pressure (dp/dt) in the normal resting state of a person sitting down is on the order of 1600 mmHg/sec and that pressure is exerted at mitral valve when the valve is closed. In contrast, the tricuspid valve on the right side of the heart, when closing, experiences only about one fifth the magnitude of the instantaneous pressure experienced by the mitral valve and on the order of a differential pressure (dp/dt) of about 350 mmHg/sec.

Although both the tricuspid valve and the mitral valve are atrioventricular valves, differences in size, structure, position and shape, and most importantly the size of the tricuspid valve requires that a specially designed replacement prosthetic valve for the tricuspid valve be different than that for a mitral valve. Also, because the physiology of the patient and the fluid dynamics of blood flow for the valves are different, unique design challenges must be overcome and different surgical methods employed.

Valve replacement may be necessitated by disease, injury, or purely by aging. For decades, surgical methods of valve repair or replacement required open chest surgery, stopping the heart, attaching a cardiopulmonary bypass machine, and surgically opening the heart to access the diseased valve. Even when successful, the surgery required a lengthy hospital stay and carried the risk of numerous complications that were frequently fatal. These drawbacks led researchers and clinicians to search for a less invasive procedure for heart valve replacement. Catheter-based interventional procedures, such as the placement of stents to expand clogged arteries, were well known for minimally invasive procedures in cardiology at the time and researchers began to examine the potential to replace defective heart valves using a catheter-based delivery system.

An artificial valve was first successfully implanted using a catheter by Andersen in 1989 in an animal model. The ability to use a catheter-based delivery system would also make valve replacement surgery available for a large number of patients who would otherwise have been disqualified based on the existence of other conditions known as "comorbidities" that put the patient at a high mortality risk from surgery under cardiopulmonary bypass. Over the years, other advances improved valve replacement procedures. In September 2000, Bonhöffer implanted a glutaraldehyde preserved bovine jugular valve using a platinum-iridium stent to support the valve at the distal end of a 6 mm catheter, into a porcine bioprosthesis within a pulmonic valved conduit that was dysfunctional in an 11-year old child. This was the first catheter-guided valve implant in a human. Cribier followed that in 2002 with implants in the aortic position using a balloon expandable replacement valve having a valve fabricated from animal tissue contained within a stainless steel stent support structure.

A series of replacement valves for the semilunar valves, the pulmonary valve and the aortic valve, using a valved stent design followed in the next decade until the use of these types of replacement valves and minimally invasive procedures for their delivery became routine and used worldwide to replace defective native valves. Valved stents for the valves where blood flow enters and exits the heart, the aortic and pulmonary valves, are now available in many different designs, and the in last few years new developments for the interchamber or atrioventricular valves, the mitral valve and tricuspid valve, are currently being tested.

Minimally invasive, catheter-based techniques were also developed for valve replacement procedures to allow access to different valves in either direction relative to blood flow, i.e. by "retrograde" means that advance the catheter in the opposite direction to blood flow, or by "antegrade" means that advance the catheter in the same direction as blood flow. Access to the tricuspid valve, whether transluminal or transatrial (a beating heart surgical procedure) is typically antegrade.

When the tricuspid valve becomes dysfunctional and unable to close properly, the capability of the heart to provide adequate unidirectional blood flow is lost. As the right ventricle (RV) pumps to move a volume of blood to the lungs, some fraction of the blood volume reverses direction and returns to the right atrium (RA) causing retrograde blood flow through the inferior vena cava (IVC) to the liver, kidneys and lower limbs, as well as toward the brain through the superior vena cava (SVC). The severity of the regurgitation can be graded from trivial, to mild, to severe, to massive and torrential. Severe regurgitations are a serious condition that also result in inadequate blood return to the heart. The liver suffers and develops what is termed cardiac cirrhosis (in effect liver cirrhosis), generalized edema and ascites, serous fluid accumulation in the abdominal cavity, also called abdominal or peritoneal dropsy or hydroperitonia. The reduced flow of venous blood also reduces the oxygenated blood flow from lung to heart and all the tissues of the body suffer as a result.

As with other valves, incompetence of the tricuspid valve is not self-repairable, and without proper treatment, an inexorable path of deterioration leads to frailty and death. Referring to FIGS. 3A, 3B and 4 herein, published literature (Nath J et al, JACC 2004 43(3) 405-409) has shown that the prognosis for tricuspid regurgitation (TR) is very poor, the one-year mortality shown as 9.7% for patients with mild TR, 21.1% for moderate and 36.1% for patients with severe tricuspid regurgitation. The majority of patients as shown by Vahanian et al. (Eur Heart J 2012 33(19): 2451-2396) do not undergo cardiac surgery because they are considered inoperable (at high risk of mortality) with a one-year mortality of about 37%. In its severe stage, tricuspid regurgitation (TR) patients have very little choice of therapy to correct the condition. In the USA, studies have estimated that the number of yearly patients presenting with moderate to severe TR is 1.9 million and less than 8,000 yearly receive surgical treatment that may prolong their life. The numbers may be significantly larger in Europe. Stuge O., Liddicoat J., et al. JTCS 2006; 132:1258-61 (see FIG. 3A); Bernal J M, et al. J Thorac. Cardiovasc Surg. 2005; 130:498-503; Taramasso M et al. J Am Coll Cardiol. 2012; 59:703-710). TR patients become inoperable or "prohibitive-risk" patients for surgical procedures that carry for them more than a 35%-40% risk of mortality.

The worldwide number of patients in late stages of TR is estimated in the millions and growing because the disease is associated with aging. The treatment presently provided consists of diuretics and blood pressure medication that are not effective because the root problem is a dysfunctional valve. Long term, these patients tend to suffer with Right Heart Failure (RHF), severe ascites, bilateral pleural effusions, and severe peripheral edema and often require monthly treatment for thoracocentesis diuresis and paracentesis and torrential tricuspid regurgitation leading to progressive frailty, with cardiac cachexia, congestive hepatopathy, renal insufficiency, refractory ascites and pleural effusions. At this point, the quality of life for these patients is very poor and the prognosis is dismal.

Both the mitral and tricuspid valves, because of their location, and their complex structure vis-à-vis the two other valves in the heart, present many difficulties when a minimally-invasive, catheter-based repair or valve replacement is considered. Navigation through the vasculature with minimally-invasive, valve replacement delivery devices, that are necessarily large enough in diameter to carry a replacement valve, but small enough to pass through the vasculature rather than open surgery approach, may be possible. However, the delivery device profile must be engineered to be reduced in size down to approximate size of the narrowest vessels through which the device must pass to deliver the prosthetic valve to the target location inside the heart without open surgery. These delivery catheters must also have the ability to bend to form sharp angles because sharp angles are required to reach target sites for some defective heart valves.

The design challenges for a prosthetic valve require that the replacement valve is constructed to be collapsible into a smaller diameter to fit inside a catheter-based delivery device. However, limits exist on the smallest possible diameter that can be created for a replacement valve while still satisfying the structural and functional requirements for long-term performance in a patient.

Moreover, when the distal end of the delivery device containing the replacement valve reaches the target site for valve replacement, the delivery catheter and replacement valved stent, then in a contracted or collapsed state inside the delivery system, must be able to approach the plane in which the native valve exists in a configuration such that the direction of approach of the replacement prosthetic valve is perpendicular and coaxial to the plane of the defective valve. The proper delivery mechanisms to attain that attitude must be part of the delivery devices to be maximally compatible in form and function with the replacement valve and must enable specific methodologies that permit deployment of the prosthetic valve in a challenging physiological environment.

One of the major difficulties that must be overcome to create a properly fitted tricuspid valve is the absolute size and dimensions of the bioprosthetic replacement valve. In a human without valve disease, normal tricuspid valve diameters have very specific size ranges. The aortic valve in the normal adult human varies from about 18 mm to about 27-29 mm in diameter and the pulmonary or pulmonic valve is generally smaller, between about 17 to about 25 mm in diameter. The atrioventricular valves, the mitral in the left side of the heart, varies from 25 to 30 mm or 31 mm, but the tricuspid valve is generally larger than the mitral valve and is normally about 27 to about 33 mm in diameter.

Exacerbating the problem for the design of the replacement valve is the fact that the size of a valve can be dramatically affected by disease or aging. Also, aging and disease can cause material deposits within the tissues of the valve that stiffen the valve tissue and narrow the size of the valve by decreasing the diameter of the fluid pathway. This condition is called stenosis and decreases the effective size of the orifice of the valve and requires the ventricle to work harder to pump blood through a smaller orifice, requiring increased pressure to effectively pump blood, and an increasing and undesirable pressure gradient between the atrium and the ventricle. With increased pressure gradients, and even as the heart works harder and harder, decreased blood flow is the inevitable result.

Tricuspid regurgitation or tricuspid incompetence is a disease of the heart's right side atrioventricular valve characterized by the inability of the valve to close during systole, when the right ventricle contracts to expel blood from the cavity towards the pulmonary valve and the lungs. The valvular orifice remains open for most of the time and allows the flow to reverse at the level of the tricuspid valve. In fact, only a reduced amount of blood can be ejected by the right ventricle that has to markedly increase the ventricular chamber volume (size enlargement) and pressure to pass the orifice.

At present various investigators have initiated valve replacement approaches, as opposed to "repair" devices for use in the tricuspid position. However, a viable replacement valve must address tricuspid regurgitation encompass and capture the wide diameter of the annulus of the dysfunctional tricuspid valve. Atrioventricular valve regurgitation, and specifically functional tricuspid regurgitation (FTR) is common in dilated cardiomyopathy (DCM) although the leaflets of the valve remain unaffected, the expanding diameter of the annulus impedes the ability of the valve leaflets to appose each other, i.e. to reach "coaptation, to provide closure to impede the retrograde flow. Investigators have found that orthotopic implantation of a bioprosthesis into a native human valve that has expanded into an abnormal diameter through disease and become regurgitant is not possible with most of the bioprosthetic valves that have been developed for aortic, pulmonary, and mitral replacement because their configuration and size cannot encompass that dilated annulus and restore valvular function.

For this condition, the major treatment effort has been directed at so-called valve-in-valve (ViV) implantation of smaller cylindrical bioprosthetic valved stents into failed surgical porcine or pericardial bioprostheses or annuloplasty rings previously implanted. Examples include the Sapien transcatheter aortic bioprosthesis (cylindrical in sizes 21 to 29 mm) and Melody transcatheter pulmonary bioprosthetic valve (cylindrical in sizes 14 to 22 mm) that have been implanted in such failed surgical bioprostheses in both the mitral and tricuspid failed bioprostheses with relative success. Other efforts when unable to correct tricuspid regurgitation sought to alleviate many of the adverse effects of tricuspid regurgitation, such as liver cirrhosis, renal failure, peripheral edema and ascites, resorted to implants of valved stents implanted in both inferior and superior vena cavae to prevent retrograde flow and pressure in both veins that can be transmitted to all those organs.

Currently, no known prosthetic valve design is capable of encompassing, grasping and maintaining hemodynamic flow when the dimensions of the diseased atrioventricular valve annulus are greatly enlarged. Furthermore, the deposition of large valves that in the mean approach 49 mm, and some reaching diameters into the lower 60 mms, require well controlled valve guidance and release during deployment such that the valve would enter coaxially to the center of the tricuspid plane and result in grasping and securing the replacement valve to the dilated annulus surrounding the diseased valve. Thus, a special catheter having articulation that would allow a shift in direction when reaching a certain point in the human right atrium, such direction then points the distal orifice of the replacement valve to the central point of coaptation of the leaflets of the tricuspid valve.

Additionally, when such catheter has been placed within the incompetent tricuspid valve, this would allow in a completely controlled manner, the initial release of the distal orifice of the valved stent such that special features of the valved stent would deploy and initiate engagement of the soft part of the leaflet without damaging or rupturing the chordae that attach to the floating margin of said leaflet. A special device must be made that would allow then the release of the proximal configuration of the valved stent that would entrap the leaflet joints and annulus from the atrial side in a totally controlled manner, and completely under manual control and visual navigation by the operator. This sequence must be very carefully carried out to ensure that the atrioventricular stent is properly placed, without canting or inclination so that complete fit to the incompetent tricuspid apparatus is made and without the allowance of interchamber (ventricle to atrium or the reverse) passage of blood around the periphery after the valved stent is released, that is, without leakage. Moreover, it is extremely important to perform these operations as described and to keep in mind that the proximal orifice of the stent has members that must be kept away from the neighboring conduction system components of the heart to prevent heart block, that is the disturbance of the conduction system that results on the interruption of the electrical activity of the heart that energizes its contraction and relaxation leading to cessation of heart rhythm and pumping of blood—a lethal outcome unless rhythm pacing is instituted. Additionally, it should be noted that tricuspid regurgitation can be caused by cardiac pacemaker leads that restrict the function of valve leaflets, and a large number of patients exist with such condition.

Thus, it would be desirable to provide a prosthetic valve that has achieved design parameters enabling replacement of a dysfunctional valve with a valve design that achieves secure anchoring at the target site as well as improved hemodynamic properties for blood flow through the valve and in the surrounding vasculature. The prosthetic valve should restore quasi-natural valve function and must not protrude into either chamber to the extent that would cause disturbance and flow patterns (turbulence) known to lead to thrombosis and thromboembolism.

It would also be desirable to provide a delivery system to enable a minimally invasive surgical procedure to anchor a replacement valve at the target site in a patient's heart by deploying the prosthetic valve to grasp the dilated annulus of a tricuspid incompetent valve, and to encompass the entire blood flow pathway to create a stable and effective replacement valve. Ideally, the delivery system may be used in either a retrograde or antegrade approach to deliver the valve through controlled release and accurate placement at the target site. Together, the controlled release and secure placement of a bioprosthetic heart valve would minimize trauma, avoid the risk and trauma of using a heart-lung bypass machine, shorten surgery time, and create better long-term outcomes compared to existing devices, delivery systems, and open-chest surgical procedures.

SUMMARY OF THE INVENTION

The current invention pertains to restoring function to cardiovascular valves, including repair and replacement of any of the four heart valves, but particularly the placement of prosthetic replacement valves for the atrioventricular valves delivered by minimally invasive surgical techniques. The invention also includes methods using an integrated system comprising replacement bioprosthetic valves and a delivery system specially designed for methods of use with the replacement valves of the invention. The system is comprised of both the valved stent specific for a target valve, e.g. the tricuspid or mitral valve, and a delivery system also specific to the target valve. Thus, the invention is comprised of each of the two devices individually and in the complementary combination of the separate devices in respective methods of use.

The methods of the invention include techniques for controlled deployment of the prosthetic valve that are enabled by the unique design of the delivery system and the valve structure. In particular, these mechanisms enable controlled deployment and release of the prosthetic valve such that the surgeon can carefully control placement of the valve at the target site and dictate the rate of expansion of the replacement prosthesis during delivery and assure landing of the valved stent in the proper zone during implantation.

Specifically, the invention provides a prosthetic valved stent for implantation at a native valvular annulus, preferably an atrioventricular valve, comprising: a support structure, wherein the support structure is expandable from a collapsed shape to an expanded shape; a tissue valve with at least one leaflet, the tissue valve being connected to the support structure; and both superior and inferior (upper and lower) means for fixing and stabilizing the stented valve onto the valvular annulus, wherein the means for fixing and stabilizing the valved stent are located at an exterior circumference of the support structure. The fixation and stabilization of the valved stent at the native annulus can also be described having fixing and stabilizing structures at both of the atrial (upper) or ventricular (lower) portions relative to the native valve annulus. Critically, the fixation and stabilization means provide a carefully controlled profile for the overall dimension of the prosthetic including relative dimensions for height and width to control the fluid dynamics both through the orifice of the replacement valve as well as in the regions just proximal and distal to the valve where fluid dynamics and relative fluid flows affect the long-term patency, thrombogenicity, and durability of the replacement valve.

In a further embodiment, the support structure of the stented valve is self-expandable to pre-determined dimensions that are selected to match a diameter of the annulus of the dysfunctional valve. In some embodiments, the measurement of the size of the replacement apparatus for an atrioventricular valve that has become dysfunctional because of the dilatation of its annulus takes into account that the annulus will be captured along with valvular leaflet material by the anchoring, fixation, and stabilization elements of the valved stent. Functionally, these elements grasp the tissue surrounding the native annulus using a pair of structures or sets of structures that each deploy from a first position to a second position as the valve evolves from a collapsed to an expanded configuration—preferable through staged deployment of the prosthetic valve wherein the stages are structured to deploy individual elements of the structure of the valve to preferentially engage the native annulus at superior and inferior portions thereof.

Because the prosthetic valve is meant to take the place of a diseased valve that may have an enlarged annulus, the deployment of the prosthetic valve is planned to achieve dimensions substantially at the extremes of the range of motion for the diseased native structures and may be coincident with the overall structure of the valved stent moving from a collapsed or constrained configuration to the expanded configuration for final placement of the native annulus. In simple terms, because the diseased valve has become enlarged and defective through disease or injury, the replacement valve has to be large enough to fit into the size of the diseased annulus and the deployment method of the prosthetic valve has to be designed to cause the valve to fit into the space correctly. This requires special design of the valve, the deployment system, and the methods used to deploy the valve. The deployment may also rely on a change from a first temperature to a second temperature when the valve is exposed to elevated body temperatures that may activate the change in configuration of the valve from the compressed configuration to the enlarged configuration and the use of shape-memory elements built into the structure of the prosthetic valve.

The unique mechanical properties of the temperature memory alloy used in the valve structure undergo solid-state phase transformations due to increased strain or change in temperature leading to a unique strain and stress relationship that defines the shape of the valve. This response to stress is termed "superelastic" and refers to the ability of the alloy to yield to an applied stress by changing its molecular crystal structure, i.e. undergo a phase change from an austenite to a martensite phase end with the reversible elastic deformation up to 10%. The thermal response, "shape memory" is also a phase transformation due to temperature changes of the material.

In one valve design, an angle of a first grasping element at or near the distal orifice or flow entry portion of the valve stent support structure swings from a first position to a second position as the catheter's distal confining capsule stent is withdrawn and the distal or ventricle outflow orifice emerges at the environmental (blood) temperature and the most distal tips of the first the tissue-engaging element deployed radially at an angle between about 40° and 50° from the surface, preferably about 42° to about 46° as the stent structure is exposed two different body temperatures. On the ventricular side, the tips of ventricular tines are positioned to be spaced between adjacent chordae tendenae. The space formed by tissue-engaging regions and the outer circumference of the stent support structure become a cavity where the portion of the edge of the valve leaflet between chordae tendinae are captured and the stent support structure also seals against the native annulus to prevent leakage around the prosthetic valve. Similarly, as the operator further withdraws the distal capsule, the tips of the proximal or atrial grasping elements in the form of winglets are deployed to form a cylindrically crimped and annularly engaged about the native annulus together with being exposed to the environmental temperature (blood temperature) at which point the engaging elements deployed radially in the distal direction toward the tips of the distal inflow orifice at a preset angle. The angle is between 80° and 95° and preferably approximately 90° (see FIG. 5C). The atrial tines thereby form an annular skirt that rests on or proximate to the floor of the atrial chamber and exerts a grasping function thereon. The resulting gap between the superior (atrial) and inferior grasping elements will, for a given size of a dysfunctional valve and valved stent, accommodate leaflets, leaflet joints, and the native annulus in a manner to provide anchoring and ceiling around the inter-chamber orifice.

In a further embodiment, the valve expands from a collapsed to an expanded configuration according to a differential temperature gradient having a first temperature of the grasping elements at between about 0° C. and 8° C., preferably between about 4° C. and 16° C. and a second temperature for the expanded configuration, wherein, the second temperature of the grasping elements is between about 20° C. and 45° C., preferably between about 35° C. and 40° C.

It is another object of the invention to provide a method of delivering a stented valve through a blood vessel to a target native valve location adjacent to or spanning a valvular annulus, comprising the steps of: advancing a stented valve having a tissue valve with at least one leaflet and a support structure, the tissue valve being connected to the support structure, the support structure being expandable from a collapsed shape to an expanded shape, wherein the support structure has a stent frame and comprises grasping means for fixing and stabilizing the stented valve onto valvular annulus, when the grasping means are comprised of a first means for engaging an upper portion of the native annulus and a second means for engaging a lower portion of a native annulus; passing the support structure through the blood vessel with the support structure in the collapsed shape; deploying the stented valve to the desired valve location adjacent to the valvular annulus with the support structure in the expanded shape; and anchoring the stented valve onto the valvular annulus with the grasping means, wherein the grasping function is provided by a first structure that engages an upper portion of the native annulus and a second structure for engages a lower portion of the native annulus. [expand—annular skirt]

In one embodiment, the support structure of the valves stent is fabricated by a shape memory metal such as Nitinol or shape memory polymer, wherein the grasping means comprises two sets of spaced apart elements that engage the tissue proximate to the native annulus as the entire prosthetic deploys and transitions from a collapsed configuration to an expanded configuration. The deployment of the device functionally anchors the prosthetic at the target site at the native annulus. In one embodiment, the grasping function is performed by structural elements that engage tissue proximate to the native annulus as the valved stent expands from a first position at a first temperature to a second position at a second temperature. The preferred valved stent creates a cavity between the circumferential exterior of the device and the tissue. The cavity considered in a cross-sectional perspective of the native valve annulus can be viewed as being in the form of a capital "J" resulting in a toroidal cavity that captures the dysfunctional valve leaflet mass, leaflet joints and annulus.

The valved stents of the present invention have specific and predetermined dimensions to yield favorable hemodynamic flow parameters through the orifice of the replacement valve and in the atrial and ventricular spaces proximate to the valve following implantation. As described above, specific flow conditions, both desirable and undesirable are a direct result of the size, shape, overall configuration of the prosthetic valve, and particularly the width height of the apparatus as a function of the discrete the various sizes of the stented valve apparatus, including all of total height of the device, relative height of the atrial portion compared to the body of the stented valve, the difference in the size of the atrial/inflow and ventricular/outflow orifice, and these factors combined.

In a further embodiment, the method of the invention includes deploying the valved stent from a collapsed configuration constrained within the distal end of a delivery catheter, to a partially deployed configuration where the valved stent assumes a partially expanded configuration, optionally followed by phase of retained deployment wherein the valve stent achieves a partially expanded configuration at one end of the prosthetic valve and substantially complete, expanded configuration at the other end of the valve, while retaining attachment by sutures or wires deployed from the delivery system. During the stage at which the valve is partially deployed or completely deployed, the valve can be restrained from total detachment for additional positioning, followed by complete deployment with the valved stent reaching its ideal configuration and positioning at the native valve, and the delivery system in position for removal.

In a preferred embodiment, the internal dimensions of the valve have absolute and relative values that are designed for optimal blood flow dynamics. As noted above, the tissue valve diameter is selected as a function of the diseased native annulus size in a patient, as a function of the selection of the tissue valve diameter, the valved stent has a series of absolute and relative dimensions including but not limited to the total valve height, the tissue valve height, the crown diameter and a tissue separation distance that either proportionally or remains constant as a function of the tissue valve diameter. The invention includes predetermined limits on dimensions or proportions of dimensions for selected measures of critical valve structures as described in further detail below.

In a further embodiment, the deploying step is carried out by self-expanding the valved stent support structure from the collapsed shape to the expanded shape or with an inflatable balloon. In a further embodiment, the blood vessel through which the valved stent passes is one or more of the internal jugular veins, the superior or inferior vena cava axillary vein, or subclavian vein, femoral and iliac vein.

Of particular interest in the present application are techniques for the implantation of a bioprosthetic atrioventricular valve that can be collapsed and retracted or folded inside a delivery system or cannula for delivering through a less invasive intercostal penetration to the desired place, particularly in a right atrium. Thereafter, the contracted, collapsed, or crimped valve is released, expanded, separated from the delivery system, and secured to the desired location with anchoring mechanisms that do not alter the vicinal structures unduly, avoiding events such as tears or punctures that impede the implantation or long term functioning of the valve, such that the prosthetic valve is able to withstand the continued impact of blood closing the leaflets with substantial pressures without propelling or dislodging the valve out of place after implantation.

The delivery system is designed to house the valved stent in the collapsed position for delivery. The valved stent is encapsulated at the distal end of the device and has a profile diameter of approximately 35 FOD. The profile diameter is deliberately designed larger than the absolute outer diameter of the valve due to the following design criteria including, but not limited to: assuring the procedure safety, device delivery safety accuracy and consistency such that the intended landing receives the bioprostheses in a controlled manner safely, accurately and consistently and to prevent misplacement of the valved stent that may result from the undesirably rapid spring effect of shape memory metals during release from a collapsed condition to an expanded condition. Slow release as controlled by the surgeon/operator will minimize the reaction forces exerted on the diseased tissue due to the compressed and constrained valve stent rapidly expanding to the predetermined and selected diameter.

DESCRIPTION OF THE FIGURES

FIGS. 1A and 1B show a section of the heart to reveal internal structures characterizing the normal path of blood flow (FIG. 1A) in the right side of the heart, including the (1) Right Atrium, (2) Tricuspid Valve, (3) Right Ventricle, (4) Pulmonary Valve. FIG. 1B illustrates a malfunctioning tricuspid valve that allows backflow of blood (TR-Tricuspid Regurgitation) into the right atrium such that surgical intervention is indicated.

FIG. 2A shows a representation of a defective tricuspid human valve (A) and surrounding annulus (B) that is defective as the result of excessive enlargement and the resulting inability for the leaflets to coapt, thereby being unable to completely close to prevent retrograde flow. The distal portion of the chordae tendonae extending away from the inferior portion of the valve are illustrated (C). FIG. 2B illustrates use of an exact obturator ring exemplifying the abnormal dilation of the dimension of the valve (D) to a diameter of 48 mm, a dimension that precludes normal function of the heart.

FIG. 3A graphically illustrates the prevalence of tricuspid regurgitation in the United States and in the world population and illustrates the extent of under-treatment of the condition.

FIG. 5A shows the general stent geometry dictated by the support structure having the angular dimensions and distances showing individual configurations, distances, angles and absolute and relative parameters as illustrated by FIG. 5B. Specific geometries and relative relationships for components of the atrial and ventricular grasping mechanism for attachment of the valved stent to then native annulus are further illustrated in FIG. 5C and Table I.

DETAILED DESCRIPTION OF THE INVENTION

Figure 2A:
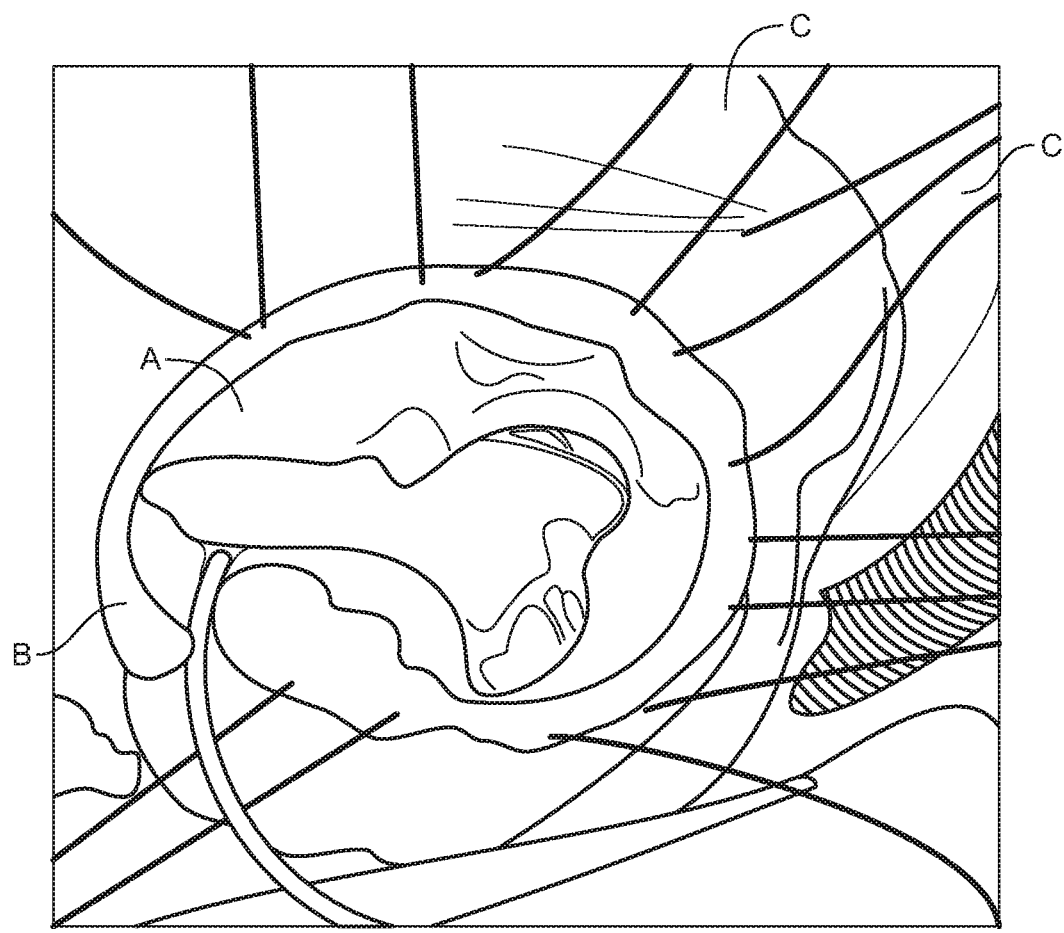
FIGS. 2A and 2B show an abnormally dilated tricuspid valve including the dimensions of the annulus of the defective valve in FIG. 2B. Specifically.

Additional objects and features of the present invention will become more apparent and the invention itself will be best understood from the following Detailed Description of the Invention, when read with reference to the accompanying drawing Figures.

Referring to FIGS. 1 to 11, a valved stent assembly and a delivery system are shown for repair and replacement of an atrioventricular heart valve using particular methods. Although the design of the valves of the present invention offer advantages even in open-heart surgical procedures, the valves of the invention are specially designed to be introduced through a blood vessel in a retrograde or antegrade manner using minimally invasive methods including transvascular, laparoscopic, or percutaneous procedures utilizing the dedicated delivery system to facilitate surgical placement of the valved stent as a prosthetic cardiac replacement valve positioned in a diseased native annulus.

The prosthetic heart valve of the present invention may be described as a valved stent assembly because it has a set of required structures: 1) a synthetic valve portion that extends substantially across the entire diameter of the support structure; 2) a stent-like support structure that surrounds and maintains the integrity of the valvular prosthesis; 3) a pre-cut polymeric mesh material covering substantially the entire inner surface of the support structure and 4) tissue-engaging structures that perform the function of grasping the tissue of the native annulus to firmly anchor the replacement bioprosthesis upon deployment. The terms "valved stent assembly" may be used herein to describe properties that are uniquely derived from the foregoing combination of structures but is generally interchangeable with the term "valved stent" that is used throughout.

The prosthetic valved stent assembly includes a valve portion fabricated from natural or synthetic tissue and has at least 2 leaflets joined at commissure portions. If the natural valve has three leaflets, the leaflets are preferably formed of sequential substantially equivalent size and shape and oriented geometrically to span the entire circumference of the valved stent. The valvular prosthesis is connected to the supporting structural frame of the valved stent at the adjacent joining margins of the leaflets at dedicated vertical structures integral with the structural frame. The valve leaflets are made from a suitable synthetic or nonhuman pericardium tissue typically harvested from ovine, caprine, bovine, or equine species and are chemically treated with buffered solutions having a low concentration (0.25%) of glutaraldehyde and glutaraldehyde derivatives that enable the valved stent to be packaged for sterilization without an accompanying storage solution. The valved stent leaflet material is formed into a valvular prosthesis assembled so that the individual valve leaflets do not directly come into contact with the structural support member of the stent but only with a microfiber cloth that covers the inner circumference of the stent structural support member. Although precise dimensions of the valved stent are given below for several discrete diameters, the valved stent may be fabricated in sizes that can extend to at least 64 mm and is great as 70 mm with equivalent dimensions as described herein for valves having smaller diameters.

The stent has a structural frame support 11 that is preferably fabricated from Nitinol alloy or other similar shape memory metal or polymer. The stent configuration is preferably laser-cut from an 8 or 10 mm hypotube and the shape is set thermo-mechanically to a predetermined orientation as shown in the series of FIGS. 5-7. The commissure bars 30, 31, 32 are also made from Nitinol alloy and support the valve commissures by attachment to the valve commissures along their length. In the embodiment of FIGS. 6A-6B, three commissure bars 30, 31, 32 at spaced at 120° apart as appropriate for a three-leaflet valve construction.

The precut polymeric fiber mesh material 23 is preferably a microfiber polyester cloth, laser cut to conform to and be substantially the size of the inner circumference of the valved stent support structure and covers the entire inside surface of the stent prior to mounting valve. In a preferred embodiment, a separate precut annular segment of the mesh material 23 is sized to cover either or both of the upper or lower surface of the annular atrial skirt and is configured to have a area at least equivalent to the entire length of the atrial tines that form the annular skirt. The mesh layer 23 of biocompatible material may be synthetic, such as polyester (e.g., Dacron®) (Invista, Wichita, Kans.), woven velour, polyurethane, PTFE, ePTFE, Gore-Tex® (W.L. Gore & Associates, Flagstaff, Ariz.), or heparin-coated fabric. Alternatively, the layer may be a biological material such as bovine, caprine, equine, and/or porcine pericardium, peritoneal tissue, pleura, submucosal tissue, dura mater, an allograft, a homograft, a patient graft, or a cell-seeded tissue.

The pre-cut mesh layer 23 may be separately attached around the entire circumference of the valved stent 10 in a single piece or may be attached in pieces or interrupted sections to allow the expandable support member to more easily expand and contract. As shown in FIG. 6B, for example, all or a portion of the annular skirt may be covered with the precut mesh layer 23. The precut mesh layer 23 may also be attached to the stent support structure 11 at intermediate points along the height thereof and may comprise a single layer formed only on the inner circumference of the valved stent support structure 11.

Preferably, the structures that perform the grasping function to anchor the bioprosthetic valve 10 in place are comprised of two separate tissue-engaging structures that are spaced apart along the height of the support structure 11 so that both atrial, or inflow, and ventricular, or outflow, portions of the valved stent assembly 10 are separately secured to both sides of the native annulus. In one embodiment, the upper and lower tissue-engaging structures are comprised of atrial and ventricular tines 18. The atrial tines 19 can be formed to collectively form an annular skirt structure 19a that rotates, pivots or swings into position upon expansion of the valved stent 10 from a collapsed to an expanded configuration. The atrial and ventricular tissue 18, 19 engaging elements are preferably cut from the hypo tube used to fabricate the stent structural support element 11. Upon rotation into the deployed configuration, the atrial annular tissue-engaging structure, the atrial skirt 19a as shown, has substantially planar upper and lower surfaces [19b, 19c??] that extend radially in approximately 90° orientation relative to a linear, central vertical axis of the valved stent 10 and rotate to form the annular ring or atrial skirt 19a to engage the tissue of the native annulus on the atrial side. The atrial tines 19 can be formed of individual inverted-V shaped winglets 21 having a proximal tip 22 and that are uniformly separated and arranged around the inflow in the form of a low profile crown 9 (dimension C, D) forming the atrial inflow orifice. Once deployed, the lower surface of the annular skirt 19a rests on the atrial side of the native annulus. Together with the ventricular tines 18, the atrial tines 19 form an external space or cavity that will capture the native dysfunctional valve leaflets and grasp the native annulus.

In the exemplary embodiments of FIGS. 5-7, twelve ventricular tines 18 are intended to grasp at the three tricuspid leaflets from the ventricular side. As with the remainder of the support structure, the ventricular tines 18 are shape-set to extend out of plane from the body of the valved stent structure 11. The number of tines is not critical as long as the number is adequate to perform the tissue-engaging function as described herein such that the grasping force is adequate to secure the native valve leaflets and prevent migration of the overall valve assembly 10.

In one aspect, implanting the bioprosthetic valve 10 to replace a dysfunctional native atrioventricular valve (tricuspid or mitral) using the valved stent assembly 10 of the present invention does not involve excising the natural leaflets or removing the native valve as is done in open cardiac surgery. Instead attaching the prosthetic heart valve 10 includes a grasping step and function that anchors the valved stent within the native valvular annulus such the native valves are permanently retracted against the walls of the native anulus. The grasping function includes retraction of the native leaflets, stable anchoring of the prosthetic in place and secure engagement by a plurality of atrial and ventricular structures the perform the grasping function without piercing or penetrating into the tissue at or proximate to the native annulus. In the presence of pacemaker or automatic defibrillator (AICD) leads going through the native tricuspid valve, as is often the case with severe tricuspid regurgitation patients, the leads must be pushed by the stent against the annulus and native leaflets without damage to the leads or interference with their function. The design of the support structure 11 allows the leads to fall within areas between the engagement structures (such as the ventricle tines 18 as described herein) such that the leads can be positioned therebetween and pressed against the native tissue without damage.

For purposes of the present invention, references to positional aspects of the present invention will be defined relative to the directional flow vector of blood flow through the implanted device. Thus, the term "proximal" is intended to mean on the inflow or upstream atrial flow side of the device, while "distal" is intended to mean on the outflow or downstream ventricular flow side of the device. With respect to the delivery apparatus described herein, the term "proximal" is intended to mean closer to the operator and handle-end of the delivery apparatus, while the term "distal" is intended to mean toward the terminal end or device-carrying end of the delivery apparatus. In the context of atrioventricular valves, the atrial direction refers to the displacement of volume with a portion of the prosthetic valve in the left or right atrium and the ventricular direction refers to the displacement of a volume with a portion of the prosthetic valve in the left or right ventricle.

The invention includes methods to deliver a stented valve through a jugular vein, subclavian vein or femoral vein comprising the steps of: (a) advancing a bioprosthetic tissue valve 10 with at least one leaflet and a support stent structure 11 through a portion of the vasculature of a patient, wherein the support stent structure 11 is expandable from a collapsed configuration to an expanded configuration, wherein the external circumference of the support stent structure 11 having at least a pair of spaced apart structures for grasping cardiac tissue proximate to the native valvular annulus and for constraining leaflets positioned on both the atrial and the ventricular side of the annulus (b) deploying the prosthetic valve at the native annulus of a dysfunctional valve by locating the valved stent assembly 10 precisely in the native annulus so that structures of the prosthetic valve assembly 10 is oriented and position to engage the annulus, followed by deployment of the valve assembly 10 achieved by expanding the valved stent structure 11 from the collapsed to the expanded configuration; and (c) securing the valved stent assembly 10 to the native valve annulus by completing the expanding step so that the valved stent 11 structure expands to the nominal dimension of the diseased valve based on a preselected size that corresponds to the measured size of the diseased native valve orifice and having both ventricular and atrial grasping elements positioned and deployed to engage to prevent dislocation and migration while providing also a sealing function to peripheral leakage along either direction of the bioprosthetic valve.

In one embodiment, the securing step is achieved by the function of grasping cardiac tissue proximate to the native annulus with components of the valve stent structure 11 comprising upper and lower elements that are configured and pivotable or swingable to form a horizontally inclined "U" or "C" or "J" configured receptacle for receiving and holding the annular and leaflet mass and for sealing the entire valve assembly 10 against the native annulus to prevent leakage and errant blood flow.

In one embodiment of a percutaneous valve implantation in an antegrade manner, that is, along with the direction of blood flow, and into the tricuspid position, the valve assembly 10 may be positioned from the atrial side, at various stages of apparatus delivery prior to competent deployment at the native annulus, thereby demonstrating that the dysfunctional tricuspid valve may be approached in antegrade fashion. In one embodiment, the delivery apparatus with a valved stent structure 11 that is retracted within the distal section of the delivery system 39 and introduced percutaneously through axillary veins, such as the subclavian vein. Once it passes through the superior vena cava and approaches the approximate center of the right atrium chamber, the distal end of the catheter 40 bearing the encapsulated valve assembly 10 is directed to the tricuspid annular plane or tricuspid valve site, the distal section is then positioned within the tricuspid valve. The catheter sheath is thereafter slowly withdrawn so as to release the valve assembly 10 out of the distal section of the delivery system 39 for example by withdrawing a portion of the catheter 40. In one embodiment, the support stent structure 11 is self-expanding and will expand incrementally as it is released from the catheter sheath. Either by motion of a mechanical portion of the delivery system 39, or by raising the temperature from the first temperature to the second temperature as described above, the valve assembly 10 is deployed. Because of the coordinated structure of the stent structure 11 is attached to the delivery system 39, depending on the antegrade or retrograde technique of delivery either a proximal or distal portion of the valve assembly 10 may first be deployed to engage either of the atrial portion or the ventricle portion of the native annulus, followed by incremental deployment of the apposing portion to most securely engage the entire valve assembly 10 at the native annulus. In this staged progression, the grasping means of the valve assembly 10 go through stages as: the pre-deployment valve, the partially deployed valve, with a swinged or pivotable distal grasping element, and fully deployed valve with both grasping elements positioned accordingly two engage the native valve annulus, to retract the diseased native valves, and to seal the valve assembly 10 against the native valve annulus.

A percutaneous valve implantation in an antegrade manner proceeds from a valved stent retracted within the distal section of the delivery apparatus and is introduced percutaneously through a vein and passed through superior vena cava or inferior vena cava. Once it passes through the heart right atrium and approaches the target atrioventricular valve (tricuspid) site, the distal section is positioned appropriately right within the annulus facing the right atrium. The catheter sheath is slowly withdrawn so as to release the valved stent out of the distal section. In one embodiment, the support stent structure is self-expanding. Thus, the stented valve will expand as it is released from the catheter sheath. By raising the temperature from the first temperature to the second temperature as described above by the body temperature, the grasping means goes through stages as: the pre-deployment valve, the partial deployed valve, a swinged distal grasping element, and fully deployed valve with both swingable grasping elements deployed.

During any step of the procedures, one may insert or utilize any imaging modalities to view the operating field. Imaging modalities may include trans-esophageal echo, trans-thoracic echo, 3D echo imaging, or an injectable dye that is radiopaque. Cinefluoroscopy may also be utilized. In one embodiment, some imaging system is deliverable through a cannula or a catheter to the operating field. The imaging system is well known to one skilled in the art.

Referring FIGS. 1A and 1B, the heart has four valves, two of which connect the heart to vasculature that delivers blood to and from the heart. Referring to FIG. 1A, blood enters the right side of the heart through two large veins, the inferior and superior vena cava, and delivers oxygen-depleted blood from the venous system to the right atrium (1) of the heart. As the right atrium (1) contracts and the right ventricle (3) relaxes, blood flows from the right atrium (1) into the right ventricle (3) through the open tricuspid valve (2). When the ventricle (3) is full, the tricuspid valve (2) shuts. This prevents blood from flowing backward into the atrium (1) while the ventricle (3) contracts. As the ventricle contracts, blood leaves the heart through the pulmonary or pulmonic valve (4), into the pulmonary artery and to the lungs where it is oxygenated.

The tricuspid and aortic valves, respectively, act as the entry gate to and the exit gate from the heart to and from the vasculature providing oxygenated blood flow to the rest of the body. These valves in their normal non-diseased state regulate the continuance of unidirectional blood through the heart. When abnormalities or disease cause malfunction and one of the four valves, the result is either incomplete blood flow entering the heart from the body, and complete blood flow within the heart and between the heart and a pulmonary system, or incomplete blood flow of oxygenated blood from the left ventricle heart to the arterial system.

Referring to FIG. 1B, a defective or dysfunctional tricuspid valve, sometimes termed an "incompetent" tricuspid valve permits abnormal backflow flow of blood in a reverse direction and into the right atrium, a condition which is termed tricuspid regurgitation (TR) and leads to the dismal mortality Figures shown in FIGS. 3 A and 3 B.

Figure 2B:
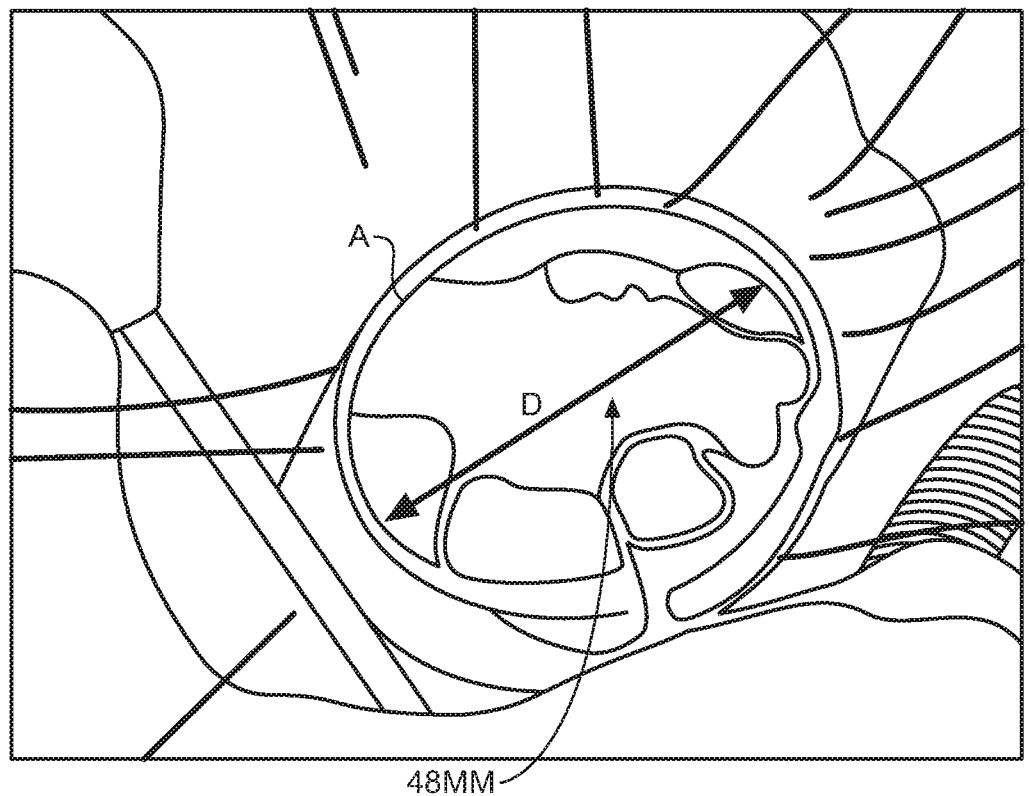

Referring to FIGS. 2A and 2B, an abnormal physiology of a tricuspid valve is shown including the dimensions of the annulus of the defective valve in FIG. 2B. Specifically, FIG. 2A shows a tricuspid human valve that is defective as the result of excessive enlargement and the resulting inability for the leaflets to coapt along their commissures, thereby being unable to completely close to prevent retrograde flow. This condition is commonly associated with a heart condition known as dilated cardiomyopathy (DCM). FIG. 2A shows a representation of a defective tricuspid human valve (A) and surrounding annulus (B) that is defective as the result of excessive enlargement and the resulting inability for the leaflets to coapt, thereby being unable to completely close to prevent retrograde flow. The distal portion of the chordae tendonae extending away from the inferior portion of the valve are illustrated (C). FIG. 2B shows measurement of the valve shown in FIG. 2A by use of an exact obturator ring exemplifying the abnormal dilation of said valve to 48 mm in diameter, an extraordinary dimension that precludes normal function of the heart.

Figure 3B:
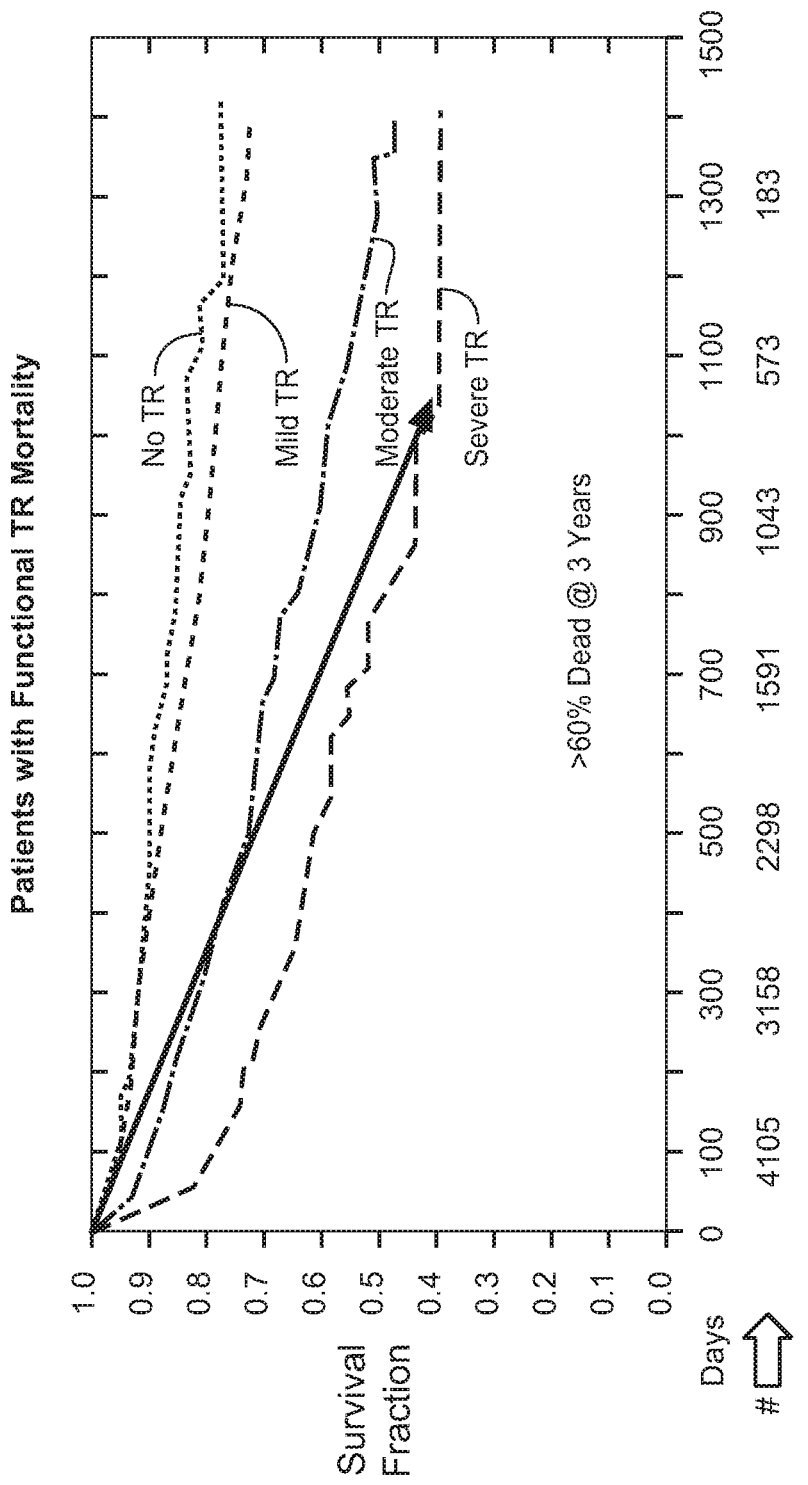
FIG. 3B graphically illustrates the relationship between selected forms of tricuspid valve dysfunction (incompetency or regurgitation) and the relation to increasing death rates over the short to intermediate term based on a study from the medical literature. Specifically, FIG. 3B reveals the rapid increase in mortality of patients presenting with tricuspid regurgitation (mortality rate of 60% within three years).

Referring to FIG. 3A, the prevalence of tricuspid regurgitation is shown in the United States population and revealing the extent of under-treatment of the condition and, in FIG. 3B, the relationship between these particular forms of cardiac valve dysfunction and increasing death rates are calculated over the short-to-intermediate term. Specifically, with respect to FIG. 3B, the data from the medical literature indicate rapid decline of patients presenting with tricuspid regurgitation (TR) and a mortality rate of 60% within three years. The graphic of the data shown in FIG. 3B, patients who our diagnosed with this disorder continually decline until death and do not tend to plateau or recover because the condition is not self-repairable by the body and the deterioration generally progresses until death.

Figure 4:
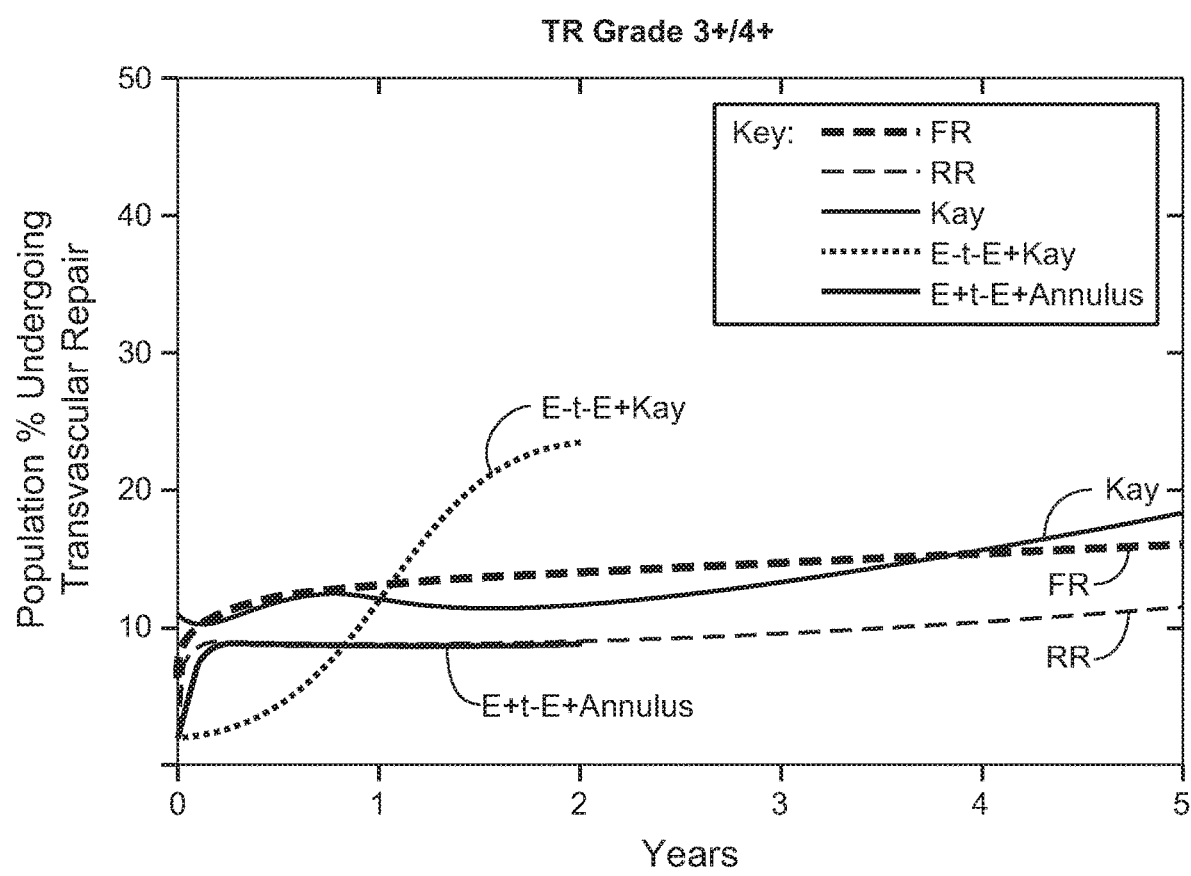
FIG. 4 illustrates the efficacy of traditional surgical repair rather than complete replacement, for incompetent tricuspid valves. The data indicate a high failure rate for traditional valve repair surgery. FR=–free repair: sutures bringing leaflets together and open-heart surgery; RR=ring repair: sutures+annuloplasty ring; Kay=specially placed sutures within the valve to bring leaflets into co-aptation; E-t-E+ Kay=Edge-to Edge approximation of valve edges plus sutures in the commissures. The lines represent the year-over-year failure of the repair indicating that a substantial majority of open heart and catheter guided repairs fail.

Referring to FIG. 4, data have been assembled to assess the efficacy of traditional surgical repair rather than complete replacement, for incompetent tricuspid valves. The data indicate a high failure rate for traditional valve repair surgery. Because of this data, valve repair procedures may be viewed as less than optimal and an improved approach would be facilitated by catheter-guided replacement devices and methods for complete replacement of tricuspid valves.

Figure 5A:
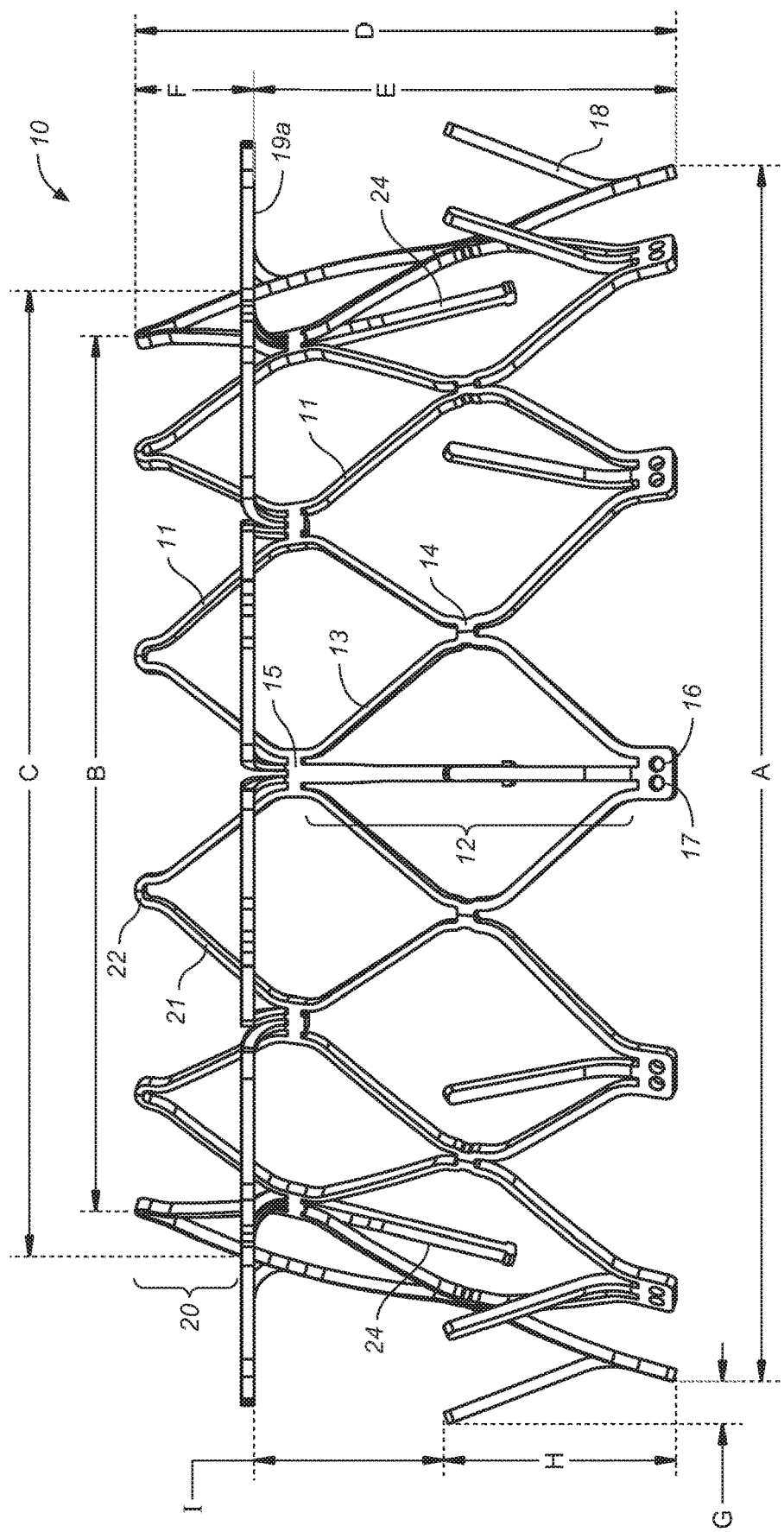
FIGS. 5A, 5B, and 5C are a valved stent frame structure for supporting the valvular mechanism of the bioprosthetic valved stent of the invention for replacement of a dysfunctional atrioventricular valve preferably by percutaneous, minimally-invasive surgery.
Figure 5B:
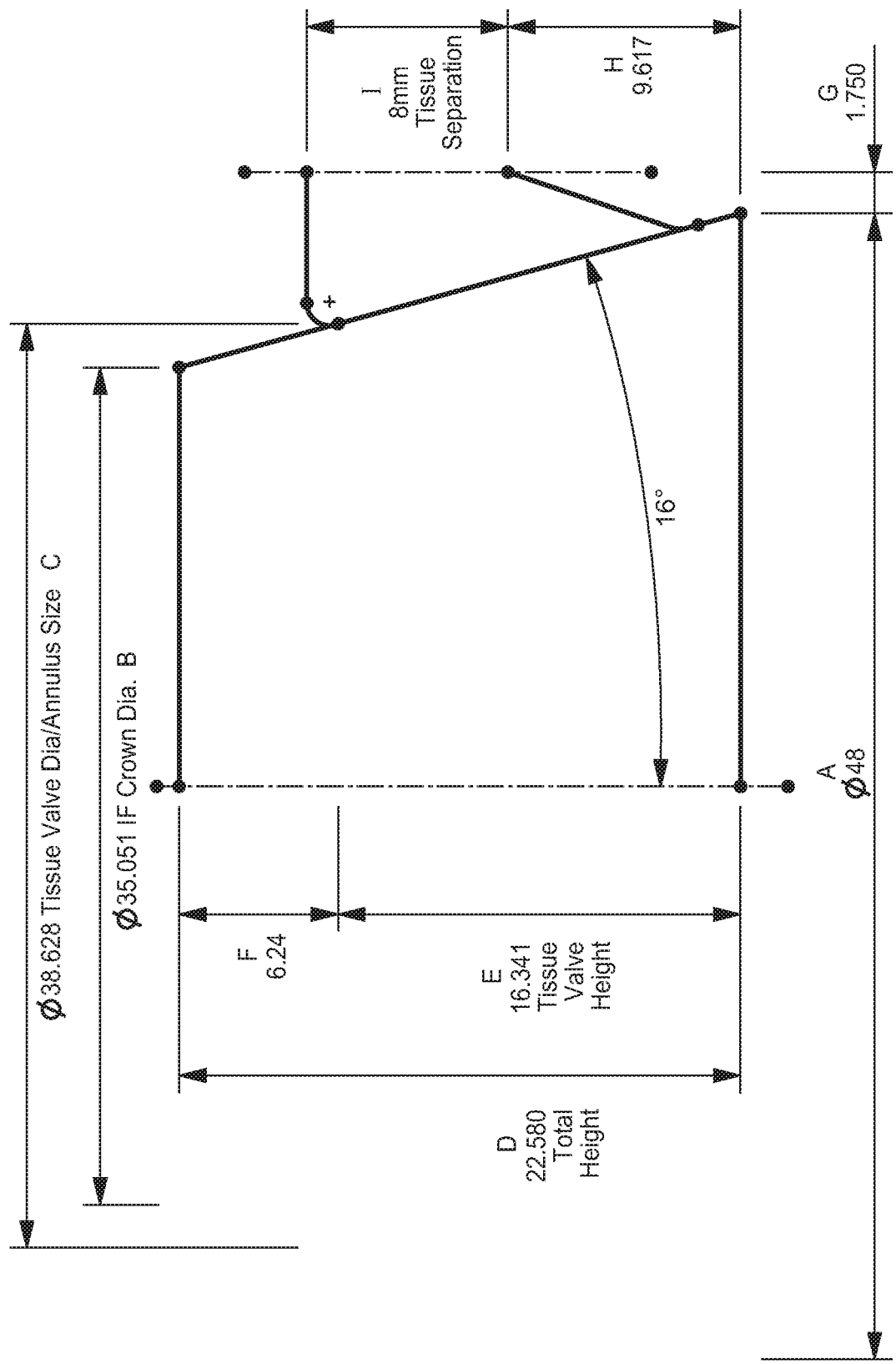
Figure 5C:
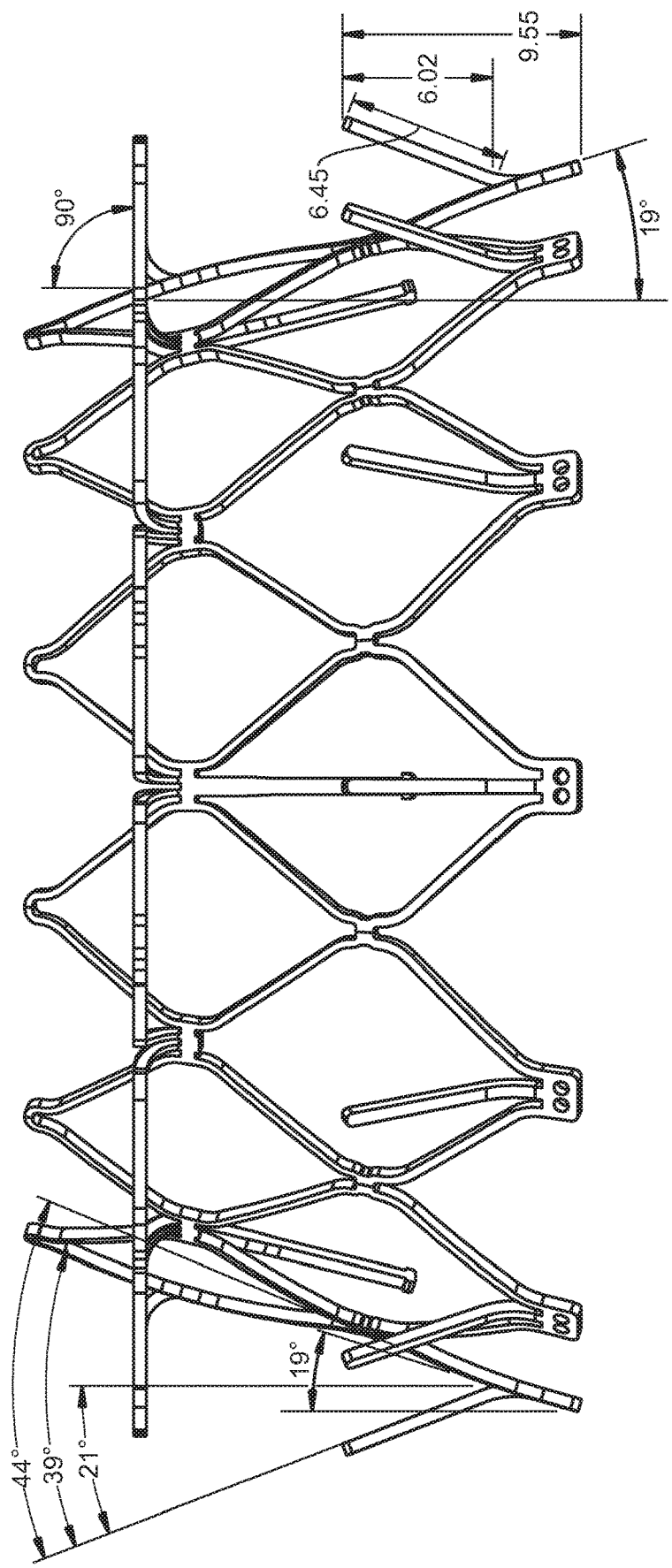
Figure 6A:
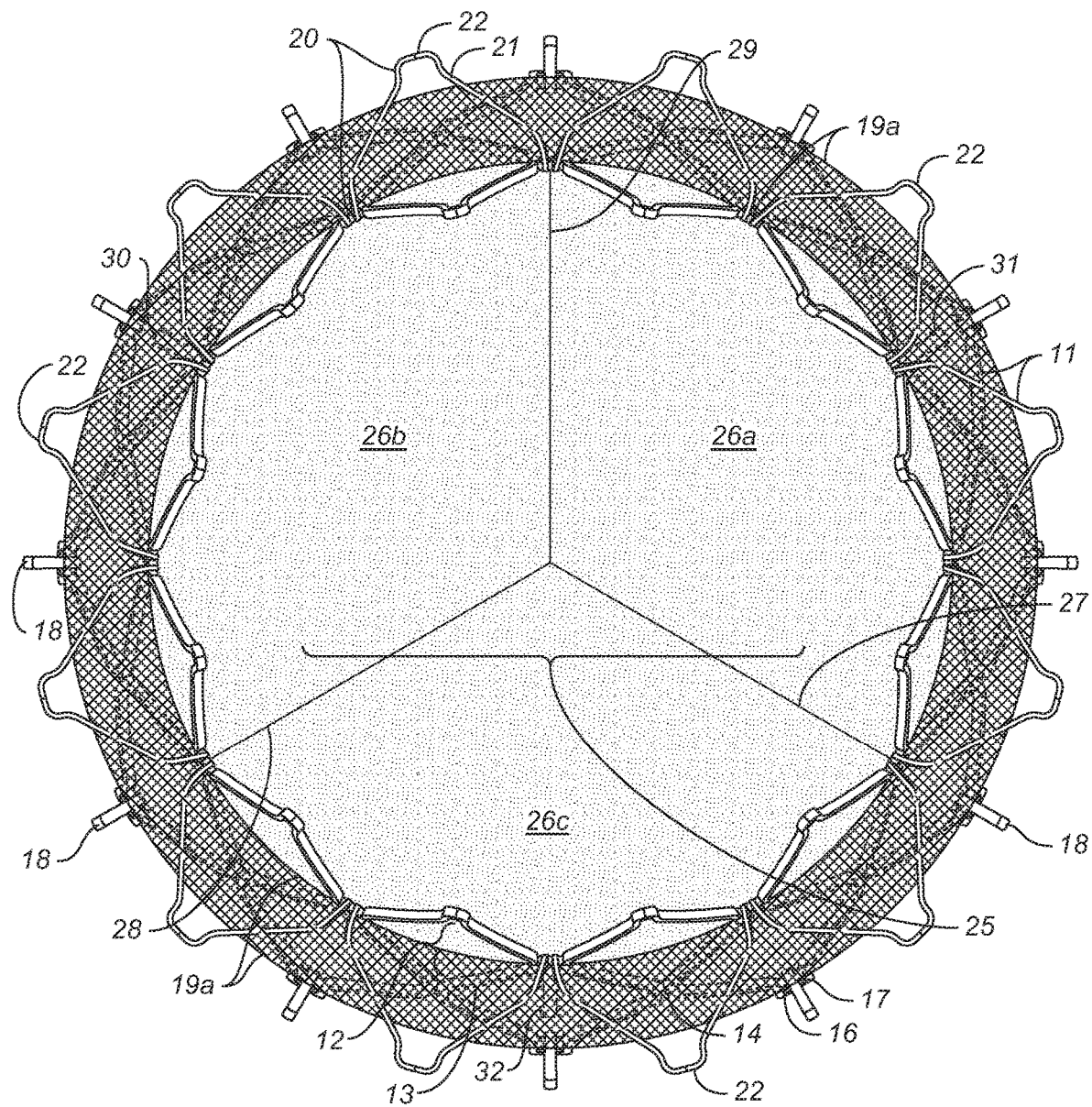
FIGS. 6A and 6B show several embodiments of a percutaneous valve wherein the valvular mechanism has been placed within the stent having the general profile of a truncated cone about the central portion of the valve assembly. Because of the geometrical configuration, the valved stents can be fabricated by those, expert in the art, in sizes that are generally twice the size of the normal tricuspid valve reaching to and beyond the diameters of annuli found in patients presenting with TR, that is larger than 48 mm and into the 60 mm range.
Figure 6B:
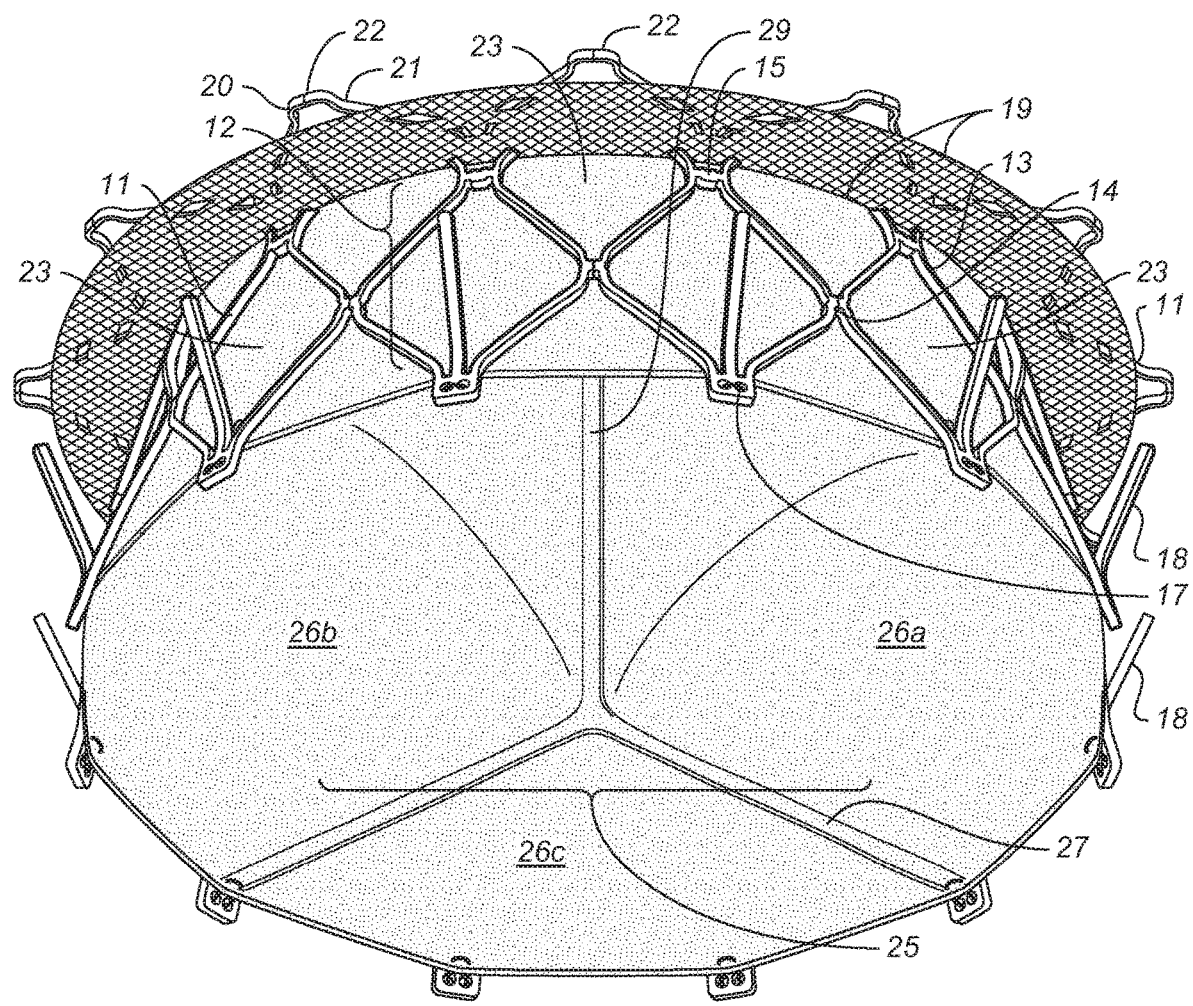

Referring to FIG. 5A-5C, a valved stent 10 has a structural frame support 11 acting as the structural foundation of the assembled structure and containing the valvular mechanism (see also FIGS. 6-7 below) of the valved stent 10 invention for replacement of a dysfunctional atrioventricular valve by percutaneous, minimally-invasive delivery. The valved stent 10 geometry is specially designed such that, when the valved stent 10 is in the expanded configuration, a truncated cone profile is created such that the superior flow entry opening or upper proximal orifice or atrial portion [B/C] of the valved stent 10 structural frame support 11 has a minimal height dimension [F], extremely low profile relative to the diameter of the valvular prosthesis [A, B, C], and such that the inflow orifice [B/C] is smaller in diameter than the inferior, lower or ventricular exit flow opening or distal orifice [A].

The specific design of the components of the valved stent 10 are based on the low profile configuration of the structural frame support 11 relative to the diameter of the valvular prosthesis [A/B/C], which is in turn derived from and dependent on, the predetermined distances, proportions of distances, angles and dimensions of the structural elements of the structural frame support 11 that yield superior flow dynamics as blood passes through the valved stent 11 and is subjected to differential pressures on both sides of the stent assembly 10. Specifically, the total dimensions of assembly 10 has a low ratio of the overall height [E/D] of the structural element of the valved stent structure 11 relative to the diameter of the tissue portion of the valve assembly 10 such that differential pressure (dp/dt) is reduced and turbulence both proximal and distal to the stent assembly 10, i.e. that in the space of the atrium immediately proximal to the valve assembly 10 and distal to the valve assembly 10, i.e. that in the space of the ventricle.

In addition to providing a central truncated cone support structure for the valve tissue 18 element of the prosthesis, the structural elements of the structural frame support 11 provide support for, and are integrally connected to, first and second tissue-engaging elements that grasp tissue on both of the atrial and ventricular side of the native annulus and form a cavity therebetween and seal engagement with the native cardiac annulus. Upon complete deployment of the valved stent 10 to the expanded configuration, the final position of the pair of tissue-engaging structures and the external circumferential area of the valved stent frame 11 form a toroidal cavity that encloses the native valve leaflets and brings the entire valved stent assembly 10 in conforming and ceiling engagement with the interior annular circumference of the native valve annulus.

The valved stent assembly 10 is comprised of a stent structural frame 11 that has individual diamond-shaped subunits 12 generally into circumferential, overlapping rows and fabricated from a shape memory tubular material from which a predetermined and pre-designed amount of material has been removed along a length thereof thereby allowing the support provided by the stent structural frame 11 to transform from a collapsed tubular or shape to an expanded configuration, which may be cylindrical or is preferably where the proximal/atrial or inflow orifice is smaller than the distal/ventricle or outflow orifice.

The individual struts 13 of the structural frame assume a predetermined configuration by virtue of the thermally set shape memory properties of the material from which the structural frame support 11 is fabricated. The individual struts 13 can be joined along a length thereof at a joint 14 that are equally spaced along the length of the individual struts 13 that form an individual diamond-shaped subunit 12 of the structural frame support 11. In the atrial or upper/superior dimension [H] of a subunit 12 of the structural frame support 11 the individual struts 13 are joined at an upper hub 15 that is also preferably joined to a plurality of atrial tines 19 that are positioned circumferentially around substantially the entire upper interior surface of the valve stent structure 11. In the embodiment of FIG. 5A, the atrial tines 19 may be fabricated to define an inverted V formation similar to the structures forming the crown 20 and are rotatable about a circumferential axis of the structural frame support 11 proximate to upper hub so that the annular skirt 19a formed from the plurality of atrial tines 19, and the entire construction of the crown 20 are substantially co-linear with the other structures of the structural frame support 11 when the valve assembly 10 is in the collapsed configuration and rotate in the expanded configuration to be deployed radially outward at an angle between approximately 80° and 100° and preferably approximately 90° relative to a vertical central axis of the valve assembly 10.

Referring to FIGS. 5A and 5C and Table I below, the dimensions, relative dimensions, angles as specified show one preferred embodiment of the valved stent assembly 10 upon deployment with the above dimensions, angles, and proportions defined by the structural frame support 11 upon deployment and assumption of the fully expanded configuration.

At the upper end of the structural frame support 11, the crown 20 extends above the circumferentially extended annular atrial skirt 19a after deployment. The annular atrial skirt 19a acts as a first tissue-engaging structure that preferably rests on the atrial floor in the expanded configuration of the valved stent 10 after deployment. The crown 20 is comprised of a series of crown subunits 21 each having an atraumatic tip 22 at the uppermost end such that the entirety of the crown 20 maintains a low profile defined by dimension F such that no structure extends substantially into the right atrium. A plurality of crown subunits 20 are comprised of crown struts 21 that define a space between the atraumatic tip 22 and the remainder of the structural frame support 11 that is comprised of an opening that can be traversed and engaged by release wires (see FIGS. 8A-8C and 9 below). Maximum heights for the crown 20 above the atrial skirt 19a are described in Table I.

At the lower/inferior or the ventricular portion of the valved stent assembly 10, ventricular tines 18 are integrally formed with a lower hub 17 that joins the individual struts 13 at the distal or ventricular portion of the structural frame support 11. The lower hub 17 may have openings 16 that traverse the body of the lower hub 17 and may receive sutures or other attachment structures (not shown). The ventricular tines 18 are preferably linear barbs attached to the lower hub 17 and that deploy radially to extend away from the lower hub 17 when the valved stent 10 expands from the collapsed to the expanded configuration upon deployment. Each ventricular tine 18 acts as a second tissue-engaging structure that extends away from the stent structural frame number 11 to engage tissue of the native valve annulus to anchor the valve assembly 10 in place.

Preferably, a plurality of ventricular tines 18 are formed from an equal plurality of lower hubs 17 to form an array of ventricular tines 18 that perform the grasping function that anchors and secures the valved stent assembly to the ventricular portion of the valve annulus after deployment. The combination of the atrial tines forming the annular atrial skirt 19a and the ventricular tines 18 form a pair of the tissue-engaging structures that engage two regions of tissue proximate to the native annulus and perform the grasping function in two directions that are annular in configuration at least partially opposed to secure and anchor the valved stent 10. The gap between the tips of the tines 18 and the outer circumferential surface of the valve stent structure 11 and the underside of the annular atrial skirt 19a form a toroidal, donut-shaped cavity which will be filled with native leaflets and annular tissue while securing the valve assembly 10 such that the entire valve assembly 10 establishes a fluid sealed interface of the atrium and ventricle thereby providing both inter-chamber sealing and preventing migration of the assembly about the annulus.

As described above, the relative dimensions of the valved stent assembly 10 establish a low-profile configuration having a large valvular tissue diameter relative to the height dimension to yield superior fluid dynamics as blood flows through the body of the structural frame support 11 when the valvular mechanism (not shown) is disposed therein. As indicated in FIG. 5B, several dimensions are defined to specify the dimensions, range of dimensions, and ratio or proportion of dimensions that provide the superior fluid dynamics for one particular valve prosthesis, in this case a valved stent assembly 10 chosen for a patient whose native annulus requires a 48 mm replacement valve.

As described below, many relative dimensions of the valve assembly 10 are aspects of the present invention and yield the unique dimensional profile and superior hemodynamics however, the overall diameter of the valvular prosthesis is determined by the individual disease pathology of the patient. For each patient, a total valve size or tissue annular diameter (TAD) is obtained by Computer Tomographic Angiography (CT Scan) and Transesophageal Echocardiography (TEE) or real time three-dimensional echocardiography (RT3DE) imaging obtained from the patient. The severity of the dysfunctional valve is analyzed in the area and perimeter of the annulus and imagery or other measurement is obtained from which the numerous dimensions of the annulus are obtained, including specifically the inner diameter of the annulus of the native valve and constitutes a target site for the placement of the bioprosthetic valve assembly 10. This diameter is matched to the closest ventricular, distal or largest diameter of a selection of the available the valve assemblies 10 having a matching diameter. Tissue annular diameter sizes that fall within the discrete diameters provided for individual sizes of the valve assembly 10, based on the expandable diameter of the stent structure 11 are best fitted to the next lower size of the valve stent, thus avoiding oversizing that impacts the sinus of the aortic valve and impacts the electrical conduction system of the heart leading to potential arrhythmias or heart block. An annulus size in the patient having a diseased native valve at the inflow diameter B defines the atrial opening or orifice for blood flow through the valve stent assembly 10. The crown diameter C is the inner diameter of the annular atrial skirt 19a. The total height D is the sum of the ventricular bottom to annular atrial ring 19 plus the crown 20 height F.

Additionally, because the height of the tissue component 25 comprised of valve leaflets, e.g. valve leaflets 26a, 26b, 26c of FIG. 6A is substantially equal to the total height of dimension D, dimension D also provides a measure of the total height of the tissue component 25 and the valve leaflets 26a-c. As noted above, because the entirety of the diameter of the valve assembly 10 is comprised of the tissue component 25 of the valvular element, the diameters, dimensions A and dimensions B, also correspond to the total diameters of the tissue component 25 measured at different points of the valve stent assembly 10. The height H of the ventricular tine 18 is from the bottom of the ventricular ring to the tip of the ventricular tine 18 as it extends away from the lower hub 17. Dimension H thereby defines the height of the engaging structure that projects from the ventricular portion of the valve stent assembly 10. As noted above, together with the atrial crown 20, having a height F above the atrial tines 19, the atrial crown 20 and the ventricular tines 18 exert a paired grasping function at the tissue on both the atrial and ventricular side of the native valve annulus.

Dimension I is the distance between the atrial-oriented tissue-engaging means 19 and the ventricular-oriented tissue-engaging means 18 and provides a capturing dimension that the valve stent structure 11 uses to encompass the native leaflet mass and to engage the native annulus in sealing and conforming engagement between the valve assembly 10 and the native annulus. Dimension I ranges between 5.5 millimeters and 9 millimeters, and is preferably between 5.5-8 mm for mitral valve prostheses and between 6.5-9 mm for tricuspid valve prostheses and is substantially approximately to 7-8 mm for tricuspid valve prostheses. In the embodiment of FIGS. 5A and 5C, dimension I is a distant between the annular atrial skirt 19a and a plane formed by the uppermost tip of the plurality of ventricular tines 18. Accordingly, the distance of dimension I may be measured between the plane of the annular portion of the atrial skirt 19a and the average distance from the uppermost tip of the ventricular tines 18 considered as positioned in a single plane. As noted herein, dimension I ranges preferably between 5.5 mm and 9 mm with a range of 5.5-8 for a mitral valve prosthesis and 6.5-9.0 for a tricuspid valve prosthesis.

These distances, dimensions, and relative and absolute proportions may be summarized as follows for valved stents having dimension A of 36, 40, 44, 48, and 52 mm:

TABLE I

| Stent Size | A | B | C | D | E | F | G | H | I | A/D | B/D |
|---|---|---|---|---|---|---|---|---|---|---|---|
| 36 | 36 | 30 |  | 20.955 | 15.9 | 5.1 | 2 | 7.9 | 7-8 | 1.718 | 1.431 |
| 40 | 40 | 30 |  | 18.796 | 15.9 | 2.9 | 2 | 7.9 | 7-8 | 2.128 | 1.596 |
| 44 | 44 | 33 |  | 19.431 | 15.9 | 3.53 | 2 | 7.9 | 7-8 | 2.264 | 1.698 |
| 48 | 48 | 35.051 | 38.628 | 22.58 | 16.341 | 6.24 | 1.75 | 9.6 | 7-8 | 2.125 | 1.55 |
| 52 | 52 | 41.5 |  | 20.955 | 17 | 3.96 | 3.15 | 9 | 7-8 | 2.481 | 1.98 |

The valved stent 10 of the invention can be fabricated to have predetermined diameters of any dimension but is conveniently offered in sizes between 36 mm and 52 mm and as large as about 64 mm while maintaining the height limitations and relative proportions as described in Table I. To achieve the benefits of the low profile design, the valve assembly 10 has a total height less than 25 mm and typically between 10 and 22 mm consistent with the of the predetermined geometry and dimensions as described herein. As is apparent from the values of table I, the ratio of the dimensions of the atrial or inflow orifice, dimension B, relative to the ventricular or outflow orifice dimension A, is between 0.60-0.90 and preferably between 0.70-0.85. Embodiments of the invention having relative proportions of 0.75 may be used as a guide to fabricate valves having the dimensions as described herein for any dimension A diameter between 30 mm and as high as 70 mm consistent with the other design parameters and dimensional limitations as described herein. In addition to the specific quantitative values in Table I, all incremental values there between are included with the disclosure of this invention together with percentage proportional ratios of the above deviating from the stated values by 95%, 90%, 85%, 80%, and 75%, consistent with the overall teachings of the invention. In a particularly preferred embodiment, the valve assembly 10 has a predetermined diameter, dimension A of between 36 and 54 mm, the ratio of dimension B to dimension A is between 0.70 and 0.85, the overall height, dimension D is less than 0.25 mm, and the dimension of I comprising the gap between the upper and lower tissue engaging structures is between 5.5 mm and 9 mm.

Referring to FIG. 5C, the relative angles of the length of the ventricular tine 18 relative to the adjacent elements of the structural frame support 11 are shown. The angle of the degree of taper of the total height of the device is shown as 19°. The total taper is preferably less than 20° and greater than 1° such that the overall dimension of the support structure is non-cylindrical and has a limited degree of taper along the entire height dimension D.

FIGS. 6A-6B are top and side perspective views of the valve assembly 10 having grasping means for fixing and stabilizing the valve assembly 10 apparatus into the valvular annulus. As noted above, the complete valve assembly of the invention comprises a tissue valve 25 secured to the structural frame support 11 and having leaflets 26a, 26b 26c. The leaflets 26a-c comprise substantially the entire diameter of the stent structural frame 11 and are attached thereto, including along substantially, or along the entire height, of dimension E in FIG. 5A above. The valve assembly includes a design where the stent structure 11 and tissue component are integrated with the proximal, atrial and distal, ventrical attachment structures are used without reliance on an additional support structure or attachment ring either interior to or exterior to the structural frame support 11. This design relies on the inherent strength of the described structural design which enable the ability to collapse the valve assembly 10 down to a minimal diameter for placement in the delivery system 39 as described below. Accordingly, the stent structural frame is attached directly to native valve tissue about the exterior surface and the tissue component of the valvular prosthesis at the interior circumference without additional structure or structural material. This configuration also enables the attachment of the material 23, such as the polymeric mesh described below which also maximizes the total working diameter of the valvular prosthesis that may be dedicated to fluid flow while providing a minimum outer diameter for confinement in the catheter 40 of the delivery system 39 while simultaneously maintaining a low profile for the overall height dimension D of the valve assembly 10.

In one particular embodiment, the support structure 11 further comprises structures that grasp the tissue proximate to the native valve annulus and in the exemplary embodiment of FIG. 5A are the crown 20 and atrial tines 19 grasping means for fixing and stabilizing the heart valve apparatus onto the native valvular annulus. The important elements of the grasping function are provided by structures that are spaced apart along the body of the grasping means comprises a plural pair of inferior and superior tissue-engaging spaced apart and located at the exterior, upper atrial and lower ventricular outer circumferential surface of the stent structural frame 11 and configured as swingable to form a generally "J" or "U" or "C" shape receptacle (outwardly) for receiving and holding the annulus.

In a further embodiment, the stent surface portion 24 of the "C" shaped receptacle 23 is uniformly substantially or entirely lined with biocompatible material 23, such as a fiber mesh or other biocompatible polymer that is not reactive with blood or blood constituents. The lining of the inner surface with material 23 serves to support the inner pericardial wall of the stent structure 11 and to seal the space between the atrial tines 19 and the area proximate the outer surface of the valve assembly 10 and the edge of the native valve annulus to prevent blood seepage or enhance local blood clotting thus maintaining separation of both superior (atrial) and inferior (ventricle) chambers of the heart. The lining material 23 is generally hydrophilic and may be selected from a group consisting of weaving of micro-fibers of esters of polymers of ethylene, silicone, polyurethane, hydrogel, fabric, and other biocompatible polymers known to those skilled in the art.

The grasping function is preferably achieved when the atrial tines 19 extend to and axially straight position (a first position) that is substantially perpendicular to the axis of blood flow through the valve 25. Because the atrial tines 19 are crimped within the distal catheter capsule when the valve apparatus is in the collapsed configuration during the delivery stage. As the valved stent is allowed to completely deploy from the capsule 50 (see FIGS. 8 and 11), the atrial tines 19 forming the annular atrial skirt 19a rotate by roughly 90° to reach the radially extending configuration and to engage the atrial side of the native valve annulus as shown in FIG. 7A.

The generally radial deployment of the ventricular tines 18 may be aided by exposure to the second temperature, i.e. the normal body or blood temperature. The angle of the ventricular tines 18 create a structure pivoting outwards from the outer surface of the stent, that may be from approximately 39° to approximately 44°.

Upon deployment, the atrial skirt 19a ventricular tines 18 exert paired grasping forces on the annular tissue of the native valve annulus to anchor the valved stent 10 in place by engaging the annulus at two positions and from two different directions. As described below, this deployment or actuation of the atrial skirt 19a and the ventricular tines 18 may be discrete steps in a deployment method of the invention that promotes precise and controlled placement of the valved stent 10 at the target, dysfunctional native annulus. In one embodiment, the first temperature is between about 1 and 35° C., preferably between about 4 and 20° C. In another embodiment, the second temperature is between about 20 and 45° C., preferably between 35 and 40° C.

Figure 7A:
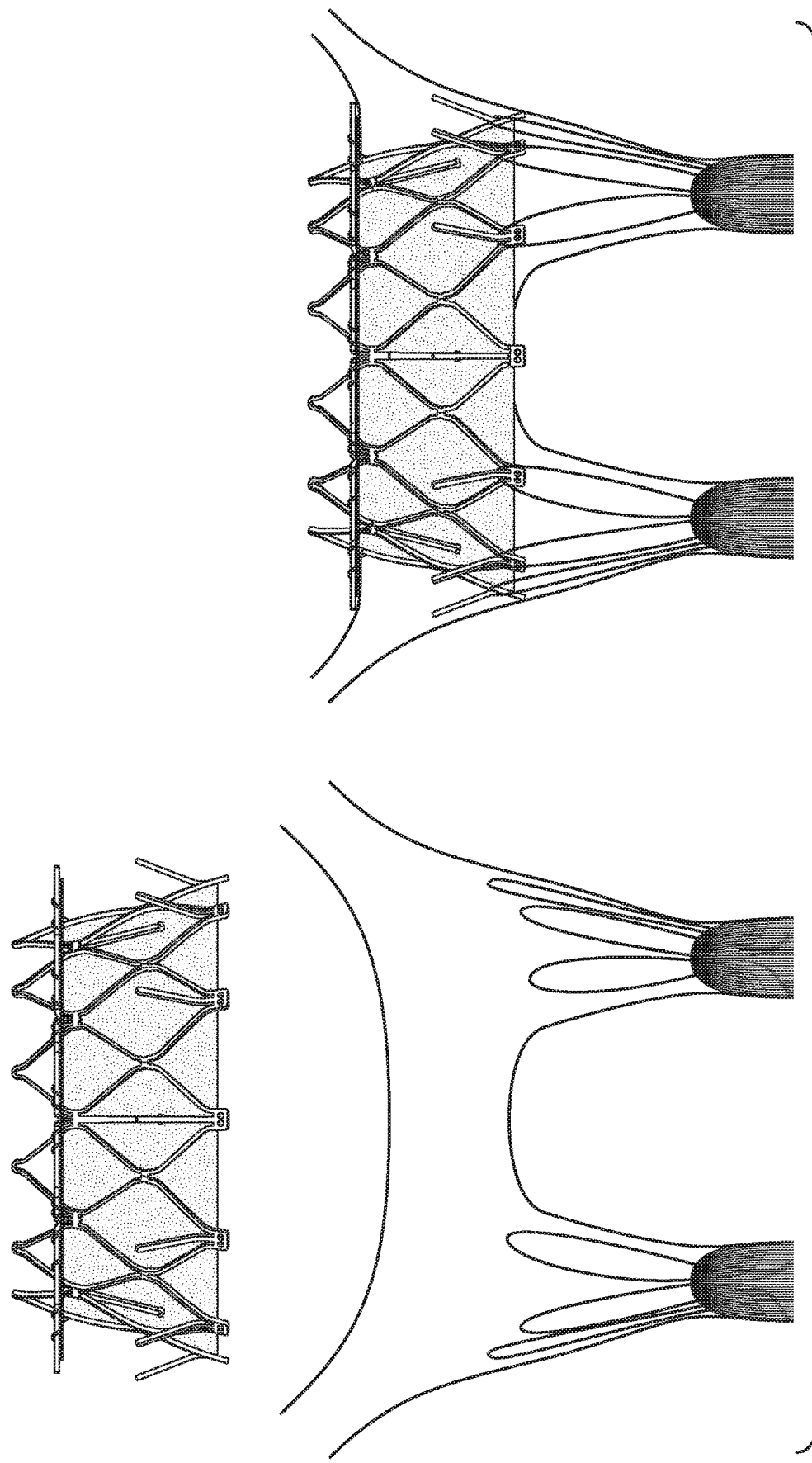
FIGS. 7A and 7B are an embodiment of the valve stent of the present invention showing the general position in which a completely expanded valve is positioned prior to engaging the native annulus (FIG. 7A (left) and the expanded valve seated at the native annulus with the distal/ventricular components of the grasping mechanism positioned and interspersed within individual strands of the chordae tendonae and with the entire assembly seated in the annulus of the native valve, showing for example, the atrial skirt in the desired relative position to the B seated on the atrial portion of the native annulus, preferably resulting in a final configuration having a low profile between the portion of the valve placed proximate to the floor of the left atrium and the chordae tendinae located between ventricular tines of the valved stent assembly.
Figure 7B:
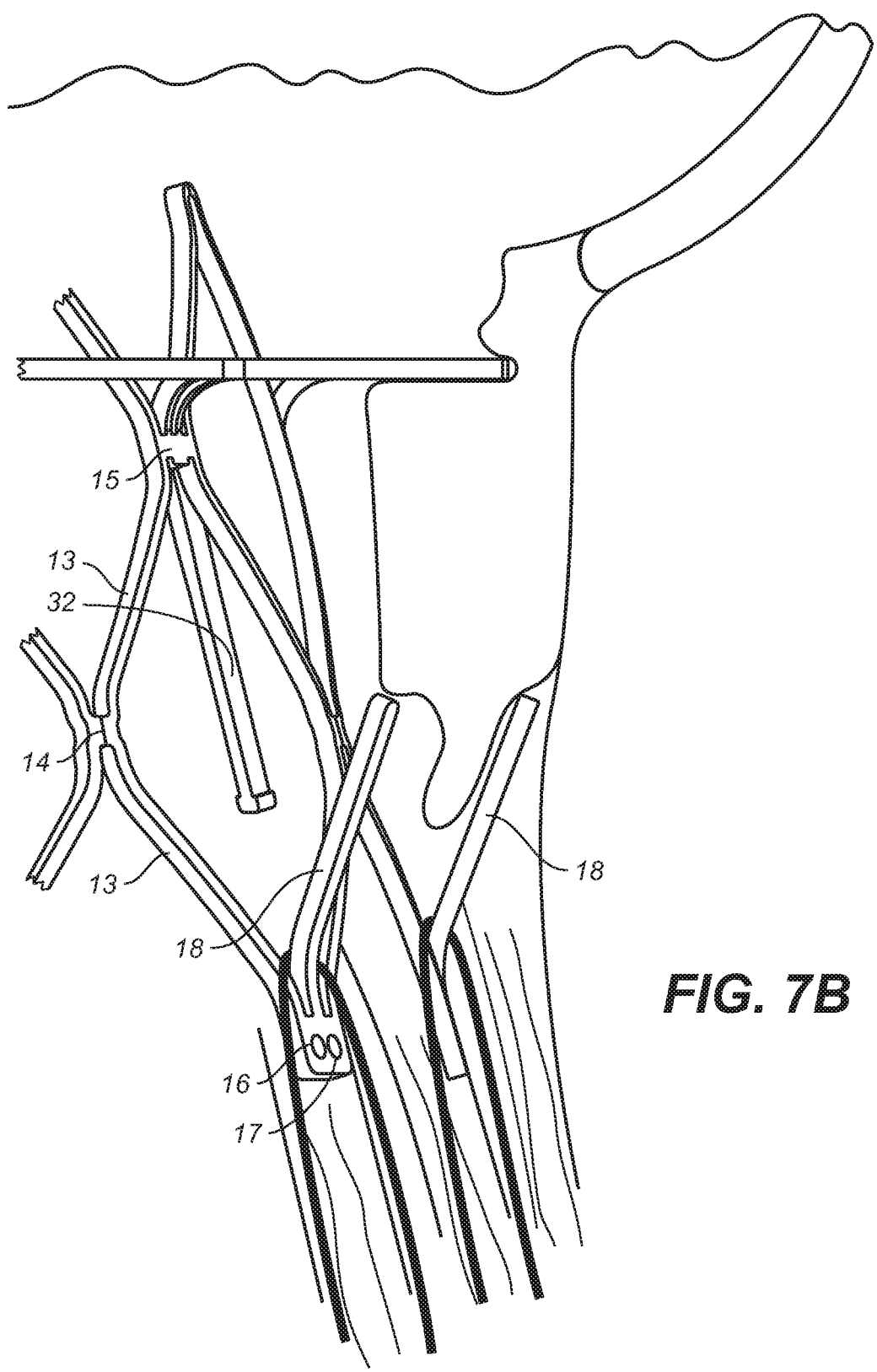

Referring to FIGS. 7A and 7B, an embodiment of the valve assembly 10 is seated in the annulus of the native valve showing the overall position of the valve assembly 10 and specifically the proximal and distal portion of the stent structure 11 relative to the valve annulus and the chordae tendonae 40 that are in turn connected to the wall of the ventricle 41. In the left panel of FIG. 7A, the valved stent 10 is shown in the expanded position and to show the sizing relative to the native valve annulus. As noted herein, the valved stent 10 of the present invention is chosen according to a measurement of the size of the dysfunctional valve in the patient and matched in size. In the right panel of FIG. 7A, the valved stent 10 is shown following replacement of the dysfunctional valve. In this example, the atrial skirt 19a engages the floor of the right atrium while the ventricular tines 18 engage the ventricular side of the native annulus such that the chordae tendonae fall between adjacent ventricular tines 18.

As seated in the native annulus, the valved stent 10 has a minimal superior profile extending into the atrium to provide superior hemodynamics and to minimize the potential for damaging contact between the bioprosthesis and the walls of the atrium during contraction. The only structure extending above the atrial skirt 19 is the tip of the crown 20, which has an inverted "V" shape and is comprised of the upper portion of the diamond-shaped strut 13 following expansion. The structural component 11 may also be comprised of vertical bars 24 that extend downward from the upper hub 15 and comprise an additional structural element to provide additional stiffness to the overall assembly, and can be used as a structural feature to attach individual portions of the valve tissue 25 including at the joining points of the individual leaflets 26 a-c. The most superior structure of the valve is the atraumatic tip 22 that defines the height of the crown 20 above the annular atrial skirt 19. As noted above, attachment to the native annulus occurs both at the superior, atrial, i.e. proximal relative to blood flow portion of the bioprosthesis by virtue of the first tissue-engaging structure, in this example the annular atrial skirt 19a as well as and at the inferior, ventricular i.e. distal relative to blood flow by virtue of the second tissue-engaging structure in this example, the ventricular tines 18. By this configuration, the grasping function of the valved stent 10 at the native annulus is facilitated by both tissue-engaging structures, one having atrial placement in one having a ventricular placement and having a discrete height (defined as dimension 'I' above) that secures the native valve leaflets and seals the valved stent 10 against the native annulus. Accordingly, the secure engagement of the valved stent 10 at the native annulus is facilitated by the tapered dimension of the structural frame support 11, the upper/atrial and lower/ventricular attachment structures of the device, and the overall sizing of the device to securely fit within the native annulus and to be anchored at the target site.

Referring to FIG. 7B, a detailed view of the attachment of the valved stent 10 to the native annulus shows close engagement of the annular atrial skirt 19a and the positioning of the chordae tendonae between the ventricular tines 18. A single subunit of the structural frame support 11 is shown having a diamond-shaped structure formed of the individual struts 13 that terminate at the upper hub 15 and the lower hub 17. The deployment of the ventricular tine is shown passing between the chordae tendonae to engage the ventricular aspect of the native annulus.

Figure 8A:
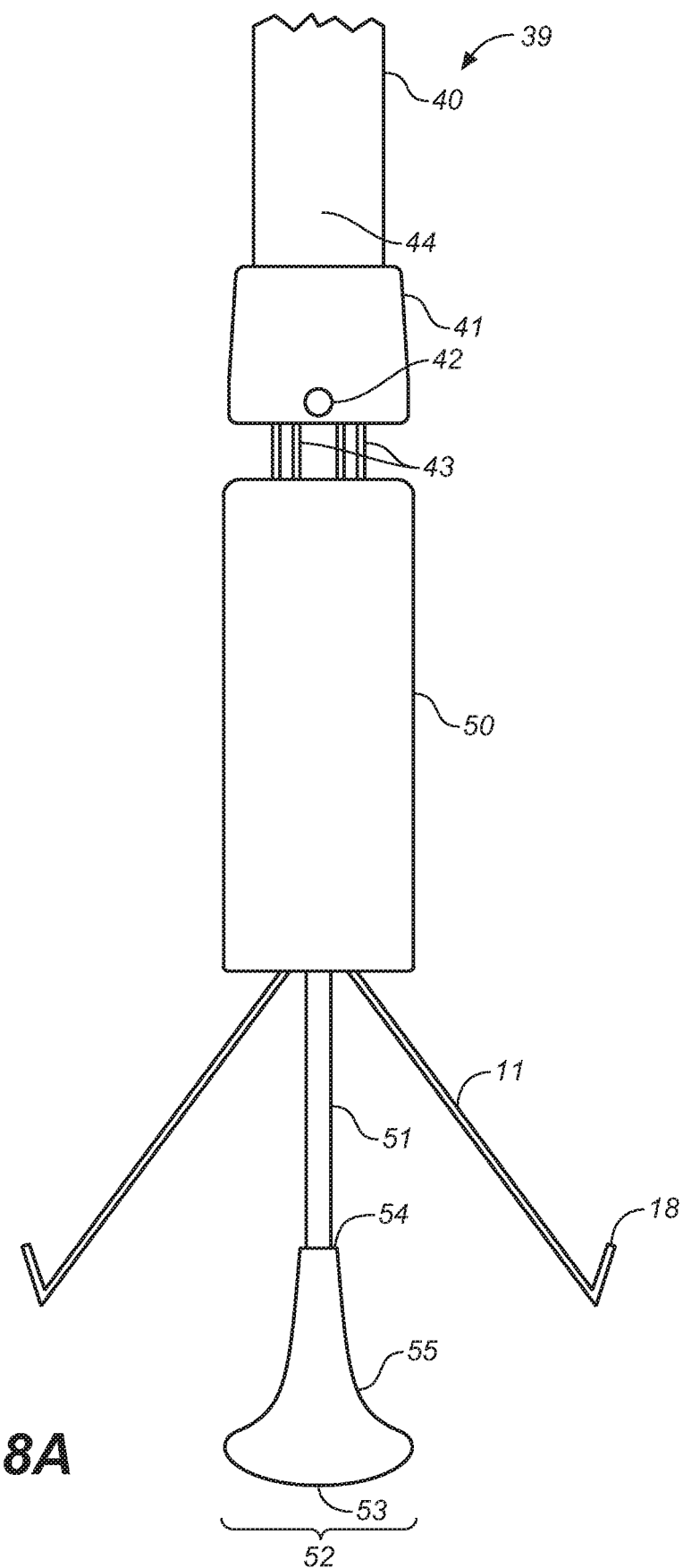
FIGS. 8A, 8B and 8C shows one embodiment of the distal end of the delivery catheter for delivery and deployment of a balloon expandable valved stent having a capsule, alignment pins, and a nose cone. For clarity, only isolated vertical portions of the structure of the stent structure (11) are shown proximal portions engaged to the deployment mechanism.
Figure 8B:
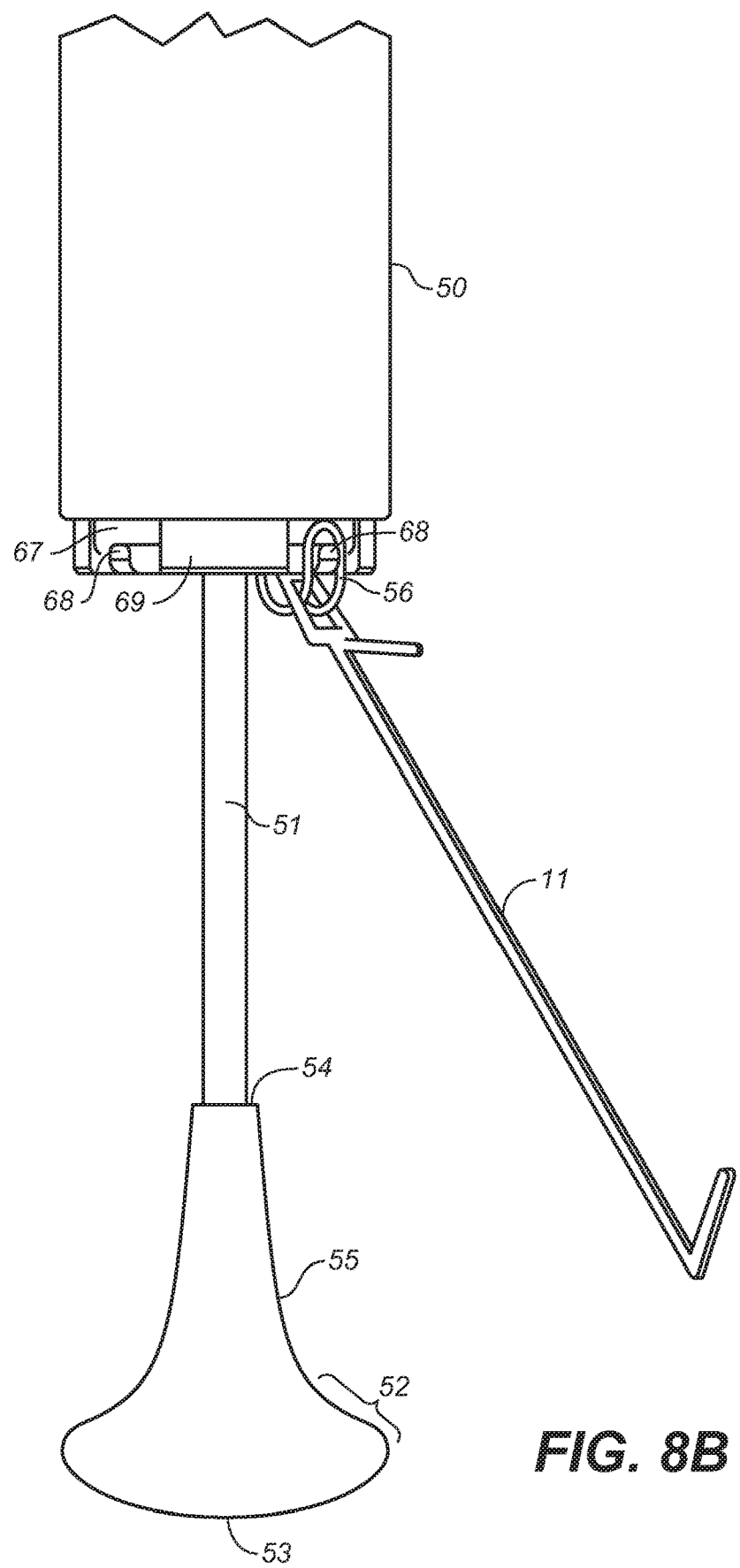
Figure 8C:
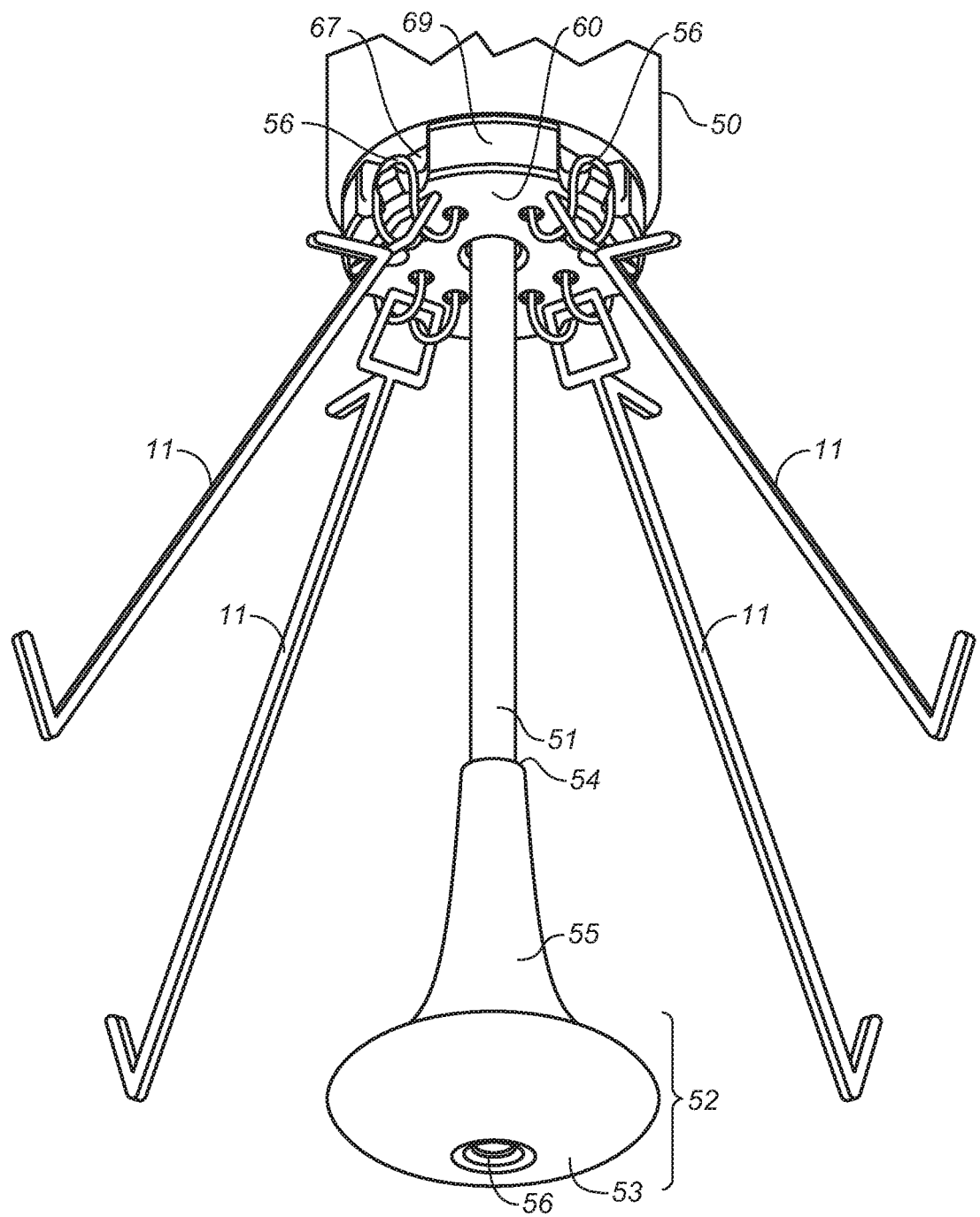

Referring to FIGS. 8A-8C, the distal end of a delivery system 39 is shown with portions of the structural frame support 11 provided to demonstrate engagement of the structural frame support 11 with the release mechanism at the distal end of the delivery system 39. The steerable catheter 40 is comprised of a hollow lumen 44 that terminates in a distal catheter hub 41 that is traversed by a pair of alignment pins 43. Although the embodiment of FIG. 8A illustrates a pair of alignment pins 43, any number of pins is contemplated as long as a steerable function is provided. A pair of alignment pins 43 permit deflection of the distal end of the steerable catheter 40 and a single plane and the ability to rotate the steerable catheter 40 allows the operator to alter the axial arrangement of the distal end of the delivery system to orient the valved stent 10 to approach the plane of the native annulus in a perpendicular fashion. A port 42 provides fluid communication that is coupled to a fluid conduit (not shown) that runs the length of the lumen 44 of the steerable catheter 40. The delivery system 39 may be comprised of capsule 50 that is positioned intermediate to the distal hub 41 and the nose cone 55. During delivery of the valve assembly 10, total diameter as defined by the collapsed structure of the stent structure 11 is contained in the collapsed configuration within the capsule 50 until the distal end of the delivery system 39 approaches the target site. The valve assembly 10 is held in place by the nose cone which is capable of axial motion relative to the steerable catheter 40 by manipulation of a bendable hypotube 51 that traverses the lumen 44 of the steerable catheter 40 and may be manipulated by the user as described in connection with FIG. 10. The wire 51 traverses the valve assembly 10 by passing through the leaflets 26 a-c and is integrally formed with the nose cone 55 by connection at an attachment point 54. The nose cone 55 has a blunt distal end 53 that is atraumatic as the distal end of the delivery system 39 traverses the vasculature to position the valved stent at the target site. In the example of FIG. 8A, the valve would be partially deployed with the stent structural frame 11 in a partially expanded configuration with the ventricular portion and the ventricular tines 18 proceeding toward the expanded configuration while the atrial portion including the atrial skirt 19a is at least partially collapsed and may be maintained within the body of the capsule 50.

Referring to FIG. 8B, the attachment/release mechanism for the valve assembly 10 is illustrated by a single member of the structural frame support 11 having a release wires 56 looped through the crown of the valved stent and engaging the tab holder 69 to maintain the collapsed configuration of the atrial portion of the valve stent while secure positioning at the target site is assured. The capsule 50 is withdrawn axially and proximally relative to the valved stent to expose the tab holder 60 and the lock wires 56 that are located at the most distal point of the lumen 44 of the steerable catheter 40.

Referring to FIG. 8C, the distal end of the steerable delivery catheter 40 is shown with four loops formed from release wires 56 that traverse the crown 20 of the valve assembly 10. Each release wire 56 engages tab 68 at the distal end of the delivery catheter 40. Each release wire 56 can be manipulated by the surgeon to loosen the engagement of the release wire 56 at the tab holder 67 to allow the release wires 56 to disengage from the tab 68. As the release wires 56 disengage from the tab 68, the release wire 56 can be drawn through the crown 20 of the valved stent releasing the valved stent from the distal end of the steerable delivery catheter 40. In the embodiment of FIG. 8C, four wire loops engage the valved stent 10 at 90° relative positions about the crown 20. Although the number of points of engagement by the release wires 56 with the crown 20 of the valved stent are not critical, at least four points of engagement with the crown 20 of the valve assembly 10 are preferred to enhance the ability to control deployment of the valve stent 10 by manipulation of the release wires 56.

The tab holder 60 has an outer circumferential surface 69 that maintains close engagement with the inner surface of the delivery catheter lumen 44. Close engagement between the external circumference of the tab holder 60 and the lumen 44 of the steerable catheter 40 ensures that the tab holder 60 remains concentrically oriented with the distal opening of the steerable delivery catheter 40 for precise positioning of the valved stent 10. The actuation of the release wires 56 occurs after the capsule 50 is withdrawn proximally to permit the release wires 56 to loosen from the tab 68. The release wires 56 traverse the body of the tab holder 60 through dedicated wire openings as described below with respect to FIG. 9B.

The diameter of the nose cone 52 is necessarily less than the diameter of the ventricular portion of the valved stent 10 so that following release of the release wires 56, the valved stent 10 can be deployed and the nose cone 52 withdrawn proximally toward through the interior of the valved stent 10 toward the tab holder 60. The nose cone 52 preferably has a curved exterior 55 that is tapered along a length to permit atraumatic traversal of the structure through the leaflets of the valved stent 10.

Figure 9A:
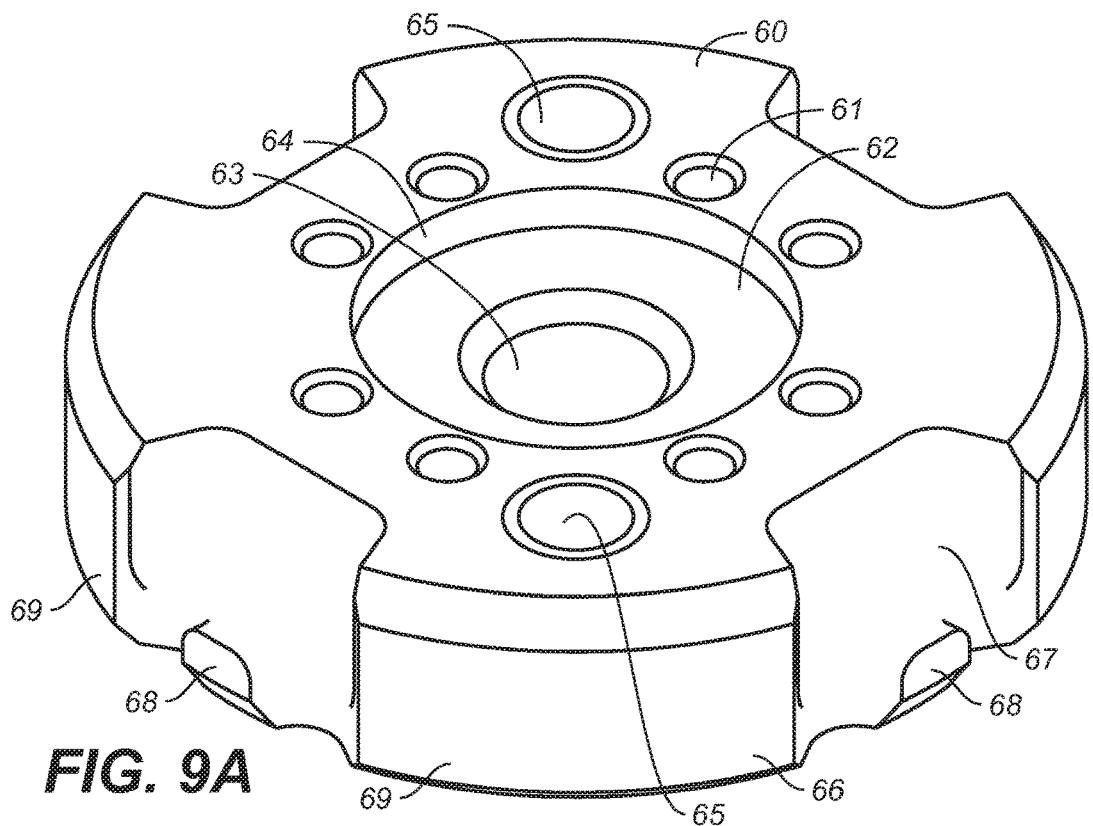
FIGS. 9A and 9B are a tab holder located at the distal end of the delivery catheter in isolation (9A) and shown as a structure that offers one approach to organize the release wires that engage the valved stent assembly and facilitate direction control of the distal end of the delivery catheter to enable controlled and directionally guided release of the valved stent assembly.
Figure 9B:
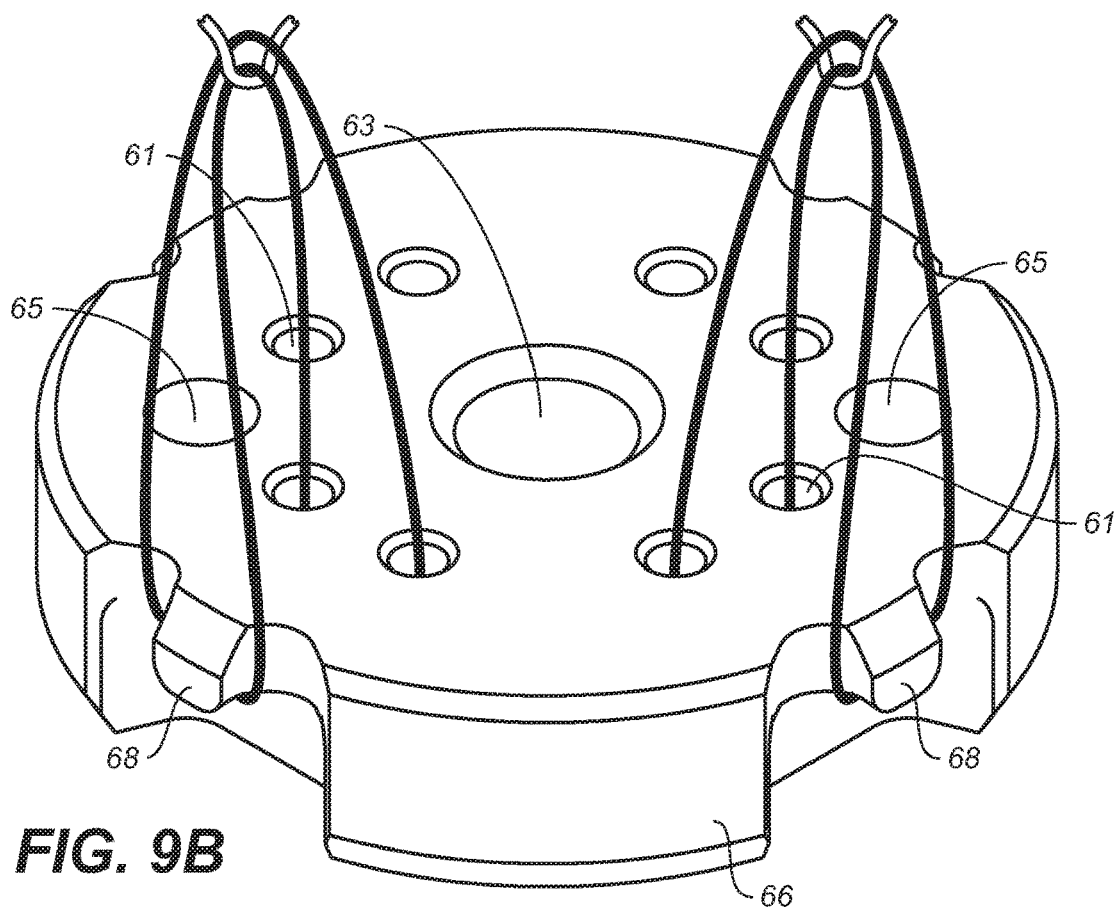

Referring to FIG. 9A-9B, FIG. 9A shows the underside of the tab holder 60 at the distal end of the delivery system 39 and shows how the release wires 56 are oriented around the central axis of the bendable hypotube 51 and the spacing away of the ports 61 for the release wires 56 away from the attachment points for the alignment pins 43. FIG. 9B also shows tabs 68 that engage the release wires 56 until loosened to deploy the valved stent. The body of the tab holder 60 is traversed by release wire ports 61 and has attachment fixtures 65 for attachment of the alignment pins 43. The central port 63 is traversed by the bendable hypotube 51 that is connected to the nose cone 52. The proximal side of the tab holder 60 has a recessed portion 62 to provide a release mechanism that enables control deployment of the valved stent 10 so that the expansion from the collapsed to the expanded configuration can be carefully controlled by the surgeon.

Figure 10:
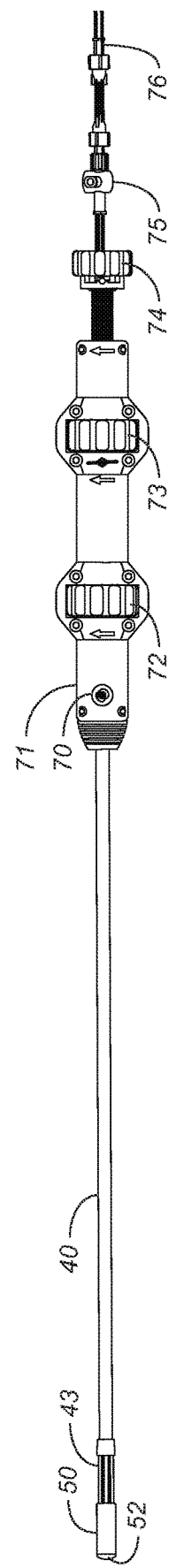
FIG. 10 is the delivery system of the present invention illustrating a handle 71 for selective operation by the surgeon to manipulate the delivery system for delivery of the valved stent as described herein.

The delivery system 39 is comprised of the distal tip assembly, the steerable catheter 40 and a handle assembly housing controls for the capsule 50, the nose cone 52, the alignment pins 43, and the release wires 56. FIG. 10 shows the entire delivery system 39 including the proximal controls enabling manipulation of the steerable delivery catheter 40. As described above, the nose cone 52 and the capsule 50 containing the valved stent in the collapsed configuration (not shown) are located at the distal end of the entire delivery system and are connected to the manual controls by the steerable catheter. The manual controls are contained in a multifunctional handle 71 that contains a flush port 70 and a control for steering the steerable catheter 40 by rotating a fixture that provides relative motion of the alignment pins 43. In a two pin embodiment, shortening either pin directs the nose cone toward the shortened pin and permits deflection of the nose cone 52 by at least 90°. The handle 71 also preferably has controls for axial motion of the capsule 59. For example rotation of a capital control knob 73 draws the capsule 50 proximally to facilitate deployment of the valve assembly 10. Separately, the control handle 71 has a fixture to control the release wires 56. For example, a knob that is rotatable around the axis of the handle 71 loosens the release wires 56 to permit deployment of the valve assembly 10.

Figure 11A:
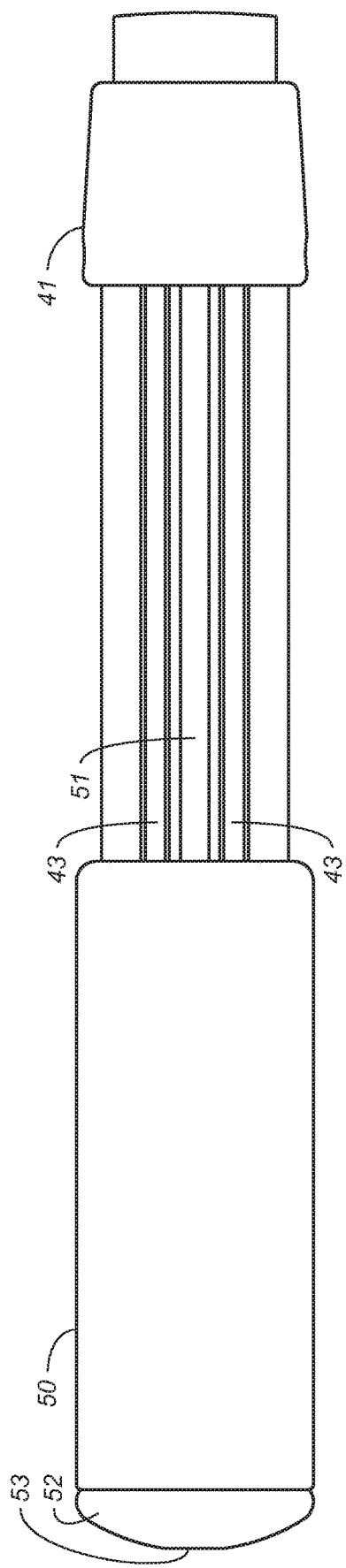
FIGS. 11A and 11B show the relative positioning of a capsule that may be employed at the distal end of a delivery catheter to facilitate maintaining the valved stent assembly in a confined configuration during delivery, followed by expansion enabled by manipulation of the position of the capsule.
Figure 11B:
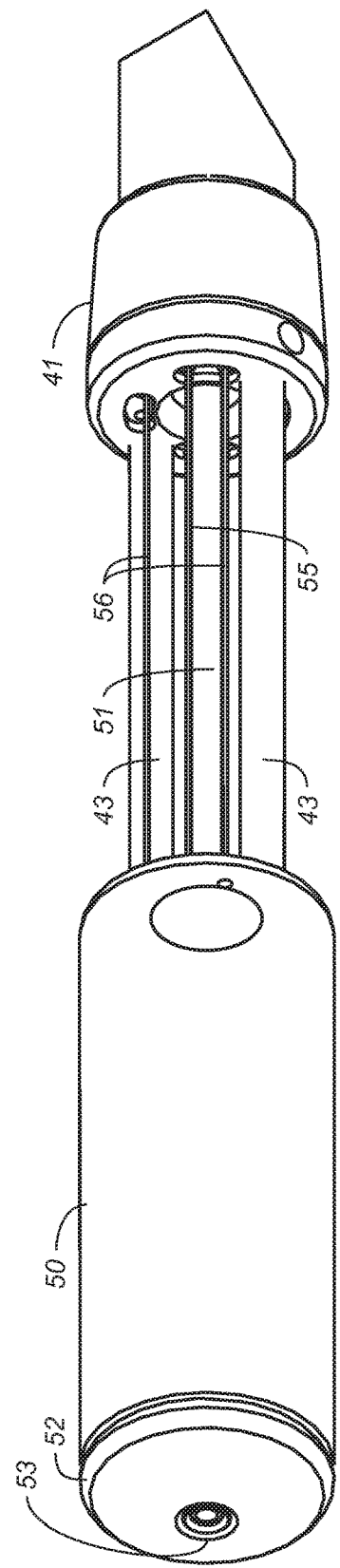

Referring to FIGS. 11A and 11B, the relative orientation of the capsule 50, the hypotube 51, the alignment pins 43 and to be release wires 56 illustrates how the capsule may be steered using the alignment pins while retaining the capability to draw the capsule 50 proximally to deploy the valved stent (not shown). As described above with respect to the alignment pins 43 shortening the length of one alignment pin 43 relative to the other causes deflection of the capsule and the ability to steer the capsule 50 containing the valved stent for deployment. As can be seen from the configuration of the delivery system, deflection of the capsule 50 is possible without altering the functionality of the hypotube 51 and the intact to the capsule 50 such that the capsule 50 can be withdrawn without affecting the orientation of the capsule relative to the axial length of the steerable catheter 40 nor affecting the tension maintained on the release wires 56. Accordingly, the capsule 50 may be partially withdrawn to deploy the ventricular tines 18 while the release wires 56 retain the attachment of atrial end of the valved stent to the tab holder 60 by means of the release wires 56. In such a configuration, the separate motion of the capsule 50 and actuation of the release wires 56 provide separate deployment of the ventricular tines from the annular atrial skirt 19. The result of this configuration is that the valve stent 10 can be deployed in a stepwise fashion such that the second tissue-engaging structure, the ventricle tines 18 can first be deployed to the ventricle portion of the native annulus to position the ventricle tines 18 between the native chordae tendonae thereby assuring secure engagement of the ventricle end of the valved stent while the atrial end of the valved stent remains captured by the release wires 56. Once the proper positioning of the ventricle tines 18, the overall configuration of the valved stent 10, and the still at least partially collapsed atrial crown 20 is assured, the atrial portion of the valve assembly 10 can be separately released to complete the deployment.

General delivery methods for catheter-based valve apparatus are known in the art. The foregoing description should be considered as modifications to procedures that are generally known. A catheter apparatus for cardiac valve bioprostheses delivery and the use thereof are well known to those skilled in the art. For example, Tu et al. in U.S. Pat. No. 6,682,558, the entire contents of which are incorporated herein by reference, discloses a catheter and a method for delivering a stent-less bioprosthetic in a body channel, the method comprising percutaneously introducing a catheter into the body channel, wherein the catheter contains the stent-less bioprosthetic at a retracted state; and disengaging the stent-less bioprosthetic out of a distal opening of the catheter by a pulling mechanism associated with the catheter structure.

Accordingly, because of the unique design, the valved stent 10 is maintained within the cylindrical housing of the capsule 50 until the distal or ventricular end of the valved stent 10 begins to emerge from the capsule and such that the inferior or ventricular tines deploy radially to an outward position (a second position) away from the outer circumferential surface of the valved stent 10. Deployment of the valved stent 10 from the delivery system can be achieved through several modalities that permit or cause the valve stent 10 to expand from the collapsed to the expanded configuration. The overall profile of the valved stent 10 may be constrained by containing the valved stent 10 within the hollow portion of an enclosure such as a lumen 44 preformed at the distal end of a delivery catheter 40. The distal end of the delivery catheter 40 may be a simple hollow space or housing for containing the collapsed valved stent 10 or may be formed of a variety of other structures to facilitate the deployment step. In a manner well-known with other implantable medical devices, the valved stent 10 may be pushed from the distal end of the delivery catheter by a pushrod or other mechanical expedient that is advanced against the structural frame support 11 of the valved stent 10. Alternatively, a mandrel may hold the stent assembly 10 in place while the outer lumen is retracted along the length of the valved stent 10 to permit expansion thereof.

In a preferred embodiment, the delivery system as described in FIG. 10 is provided with a steerable delivery catheter 40 comprised of: a catheter having a lumen 44 comprised of a braided Pebax tube and PTFE liner and may have an outer diameter of less than approximately 24 F and a length of at least 41 cm, a distal steerable region comprised of the capsule 50 and the nose cone 52 and capable of directional control and an angle of deflection of at least 75° and preferably 90° or more by manipulation of a steering mechanism. The steering mechanism may comprise any mechanical expedient that is operable from the handle 71 of the delivery system 39 and steers the distal end of the delivery catheter 40. In the embodiment of FIGS. 8 and 11, the steering mechanism comprised of the alignment pins 43. However, the alignment pins 43 may be replaced with a steerable guide wire or other equivalent to reduce the overall diameter of the capsule element constrained by the necessary diameter dimension A of the valve assembly 10. The length of the steerable region is approximately 25 mm. A stainless steel cable (not shown) may be embedded in the steerable catheter 40 for navigational control. The controlled release wires 56 are preferably made of PTFE-coated Nitinol and enable controlled release of the valve assembly 10. The combination of the fixture tab 68 on the tab holder 60 form a release mechanism comprised of the releasable attachment of the crown 20 or winglet subunits 21 having an opening therein that are traversed by the release wires 56. Accordingly, the release wires 56 runs the length of the steerable catheter 40 from the control mechanism 74 through the lumen 40, traversing the winglet subunits 21 of the crown 20 and engaging the tab holder 60 at the tab 68 of the tab holder 60. Simply loosening the release wires 56 by increasing their length releases the distal end of the release wires 56 from the tab 68 and releases the atrial portion of the valve assembly 10 once the surgeon has confirmed that the valve assembly 10 is properly placed.

The delivery system handle 71 is comprised of the following: a steering control knob 72 for directional navigation of the distal end of the steerable catheter 40. The steering control has a torque limiter to prevent damage due to the potential for over steering. A capsule control knob 73 controls initial partial release of the ventricular portion of the valve assembly 10 by retraction of the capsule 50 thereby causing at least partial expansion of the ventricular aspect of the valved stent 10 as the length of the structural frame support 11 is exposed as the capsule 50 retracts. The handle 71 is further comprised of a control mechanism for the release wires 56 that loosens the release wires for controlled deployment of the atrial portion of the valve assembly 10 and ultimately final release of the entire prosthetic at the target site. A safety pin (not shown) may be added to the release wire control mechanism to prevent unintended release of the valve assembly 10 from the distal end of the delivery catheter 40.

Echo and fluoroscopic imaging is used for navigation and any structural feature of the valve stent 10 or the distal portion of the delivery system 39 may have an added element for detection upon imaging. The distal tip of the delivery apparatus 39 may be guided into a desired configuration at the native dysfunctional annulus by rotating the steering control knob and by rotating the entire handle 71. In stepwise fashion, deployment of the valved stent 10 is achieved by first advancing the nose cone 53 a short distance from the dysfunctional native valve under fluoroscopy. Next, the capsule control mechanism 73 is actuated, for example by clockwise rotation of a knob. A safety feature may fix the position of the capsule after an initial release of the ventricular portion of the valved stent 10 by locking the capsule control mechanism 73 in place to prevent further rotation and axial motion of the capsule 50 relative to the axis of the steerable catheter 40. This retracts the capsule 50 and exposes the ventricular or outflow aspect of the implant. At this point the distal, ventricular outflow aspect of the valve stent 10 is in a substantially open configuration while the proximal, atrial inflow portion of the valved stent 10 is restrained, for example at a diameter of substantially equal to the inflow diameter dimension B by maintaining tension on the release cables 56. Final adjustments to the location of the valved stent 10 within the native valve annulus is performed, then the controlled release knob 74 is rotated to advance the controlled release wires 56. This action slowly expands the atrial inflow portion of the valved stent until the crown 20 is fully expanded in the atrial skirt 19 rotates approximately 90° into the fully expanded configuration. Additional maneuvering of the valved stent 10 can be performed by gently pushing or pulling the delivery system 39 to ensure the valved stent is seated in the proper position within the tricuspid annulus.

Next, a safety pin is pulled while simultaneously causing counterclockwise rotation of the capsule control mechanism 73, which further retracts the capsule 50. Next, the release wire control mechanism 74 is actuated, such as by counterclockwise rotation to retract the release wires 56 back into the lumen 44 of the delivery system catheter 40. The nose cone 52 is retracted by pulling the guidewire 51 such as by retraction of the proximal portion 76 of the guidewire as it extends proximally of the handle 71 at an attachment point. A Tuohy Borst adapter 75 is tightened on the guidewire catheter 51 which locks the nose cone 52 in a retracted position. At this point, the delivery system catheter 40 can be safely extracted.

In a preferred embodiment, the valved stent 10 is stored in an expanded configuration and then compression loaded into the delivery catheter 40 just prior to use by reducing the temperature of the valved stent 10 as described above. The compression loading system may be comprised of the following components: a valved stent support fixture with and ice bath; a compression cone—preferably made of Ultem® (polyetherimide); a transfer capsule—preferably made of Ultem®; a push tool—preferably made of Ultem®; and a standard compliant balloon with a syringe.

The various embodiments described above can be combined to provide further embodiments. All of the priority and related U.S. patents, and non-patent publications referred to in this specification are incorporated herein by reference, in their entirety. Aspects of the embodiments can be modified, if necessary, to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

We claim:

1. A method to deliver a bioprosthetic valve comprising:
   advancing a valve assembly through vasculature of a patient suffering from a native valve dysfunction, wherein the valve assembly is comprised of:
   a structural stent support expandable from a collapsed to an expanded shape and having an inflow orifice and an adjacent first tissue engaging structure comprised of an annular skirt extending radially from a frame of the structural stent support and about the perimeter of the inflow orifice, a having a outflow orifice and an adjacent second tissue engaging structures adjacent thereto, integrally formed with the frame, and circumferentially spaced around the periphery of the outflow orifice, wherein the frame of the structural stent support has a tapered dimension along the entire height thereof such that the inflow orifice has a smaller diameter than the outflow orifice and the tapered dimension extends between the annular skirt and the second tissue engaging structures;
   a precut mesh layer covering the interior surface of the structural stent support from the inflow orifice to the outflow orifice;
   a tissue valve having at least two leaflets and affixed about the inner surface of the structural stent support and having a height and a diameter approximately the same as the height and diameter of the structural frame support; and
   manipulating a delivery system to deploy the annular extending from the distal end of the delivery system to anchor the structural stent support about the periphery of a first side of a native valve annulus;
   manipulating the delivery system to deploy the second tissue engaging structures from the periphery of the outflow orifice to engage a second portion of the native valve annulus; and
   releasing the valve assembly from the distal end of the delivery system to sealingly engage the valve assembly to the native valve annulus.

2. The method to deliver the bioprosthetic valve of claim 1, wherein the delivery system is manipulated to deploy first tissue engaging structure at an atrial portion of a dysfunctional native valve.

3. The method to deliver the bioprosthetic valve of claim 1, wherein the diameter of the outflow orifice of the structural stent support is between 36 and 64 mm. frame support.

4. The method to deliver the bioprosthetic valve of claim 3, wherein the atrial skirt extends from the structural frame support at an angle between 85 and 95°.

5. The method to deliver the bioprosthetic valve of claim 1, wherein the delivery system is manipulated to deploy the second tissue engaging structure at a ventricle portion of a dysfunctional native valve.

6. The method to deliver the bioprosthetic valve of claim 5, wherein the second tissue engaging structure is a plurality of ventricular tines extending radially away from a plurality of hubs located circumferentially around the outflow orifice.

7. The method to deliver the bioprosthetic valve of claim 1, wherein the releasing step is comprised of causing the valve assembly to sealingly engage the dysfunctional native annulus in an expanded configuration of the valve assembly, wherein the distance between the first tissue engaging structure and the second tissue engaging structure is between 5.5 and 9.0 mm.

8. The method to deliver the bioprosthetic valve of claim 7, wherein the distance between the first tissue engaging structure and the second tissue engaging structure is between 7.0 and 8.0 mm.

9. The method to deliver the bioprosthetic valve of claim 1, wherein the releasing step is comprised of causing the valve assembly to sealingly engage the dysfunctional native annulus in an expanded configuration of the valve assembly, wherein the total height of the structural frame support of the valve assembly is less than 25 mm.

10. The method to deliver the bioprosthetic valve of claim 1, wherein the releasing step is comprised of causing the valve assembly to sealingly engage the dysfunctional native annulus, wherein the ratio of the diameter of the inflow orifice relative to the outflow orifice is between approximately 0.60 and approximately 0.90.

11. The method to deliver the bioprosthetic valve of claim 10, wherein the ratio of the diameter of the atrial inflow orifice relative to the ventricular outflow orifice is between approximately 0.70 and approximately 0.85.

12. The method to deliver the bioprosthetic valve of claim 1, wherein the releasing step is comprised of causing the valve assembly to sealingly engage the dysfunctional native annulus, wherein the diameter of the dysfunctional native annulus orifice is greater than 30 mm.

13. The method to deliver the bioprosthetic valve of claim 1, wherein the advancing step is comprised of advancing the delivery system in an antegrade fashion through the vasculature of the patient.

14. The method to deliver the bioprosthetic valve of claim 1, wherein the advancing step is comprised of advancing the delivery system in a retrograde fashion through the vasculature of the patient.

15. The method to deliver the bioprosthetic valve of claim 1, wherein the step of releasing the valve assembly from the distal end of the delivery system is comprised of manipulating a plurality of wires that traverse the delivery system.

16. The method to deliver the bioprosthetic valve of claim 15, wherein the plurality of wires that traverse the delivery system engage a crown surrounding the inflow orifice of the valve assembly and the step of releasing the valve assembly is comprised of disengaging the releasing wires from the crown.

17. The method to deliver the bioprosthetic valve of claim 1, wherein the step of releasing the valve assembly from the distal end of the delivery system is comprised of axial motion of a capsule located at the distal end of a steerable catheter and containing the bioprosthetic valve of claim 1.

* * * * *